(12) United States Patent
Hirose et al.

(10) Patent No.: US 11,490,805 B2
(45) Date of Patent: Nov. 8, 2022

(54) OPHTHALMIC INFORMATION PROCESSING DEVICE, OPHTHALMIC DEVICE, OPHTHALMIC INFORMATION PROCESSING METHOD, AND PROGRAM

(71) Applicant: TOPCON CORPORATION, Tokyo (JP)

(72) Inventors: Ryoichi Hirose, Itabashi-ku (JP); Tatsuo Yamaguchi, Warabi (JP)

(73) Assignee: TOPCON CORPORATION, Tokyo (JP)

( * ) Notice: Subject to any disclaimer, the term of this patent is extended or adjusted under 35 U.S.C. 154(b) by 420 days.

(21) Appl. No.: 16/777,927

(22) Filed: Jan. 31, 2020

(65) Prior Publication Data

US 2020/0245862 A1   Aug. 6, 2020

(30) Foreign Application Priority Data

Feb. 5, 2019   (JP) .............................. JP2019-018738

(51) Int. Cl.
*A61B 3/00* (2006.01)
*A61B 3/10* (2006.01)
*A61B 3/12* (2006.01)
*G06T 3/60* (2006.01)

(52) U.S. Cl.
CPC ............ *A61B 3/102* (2013.01); *A61B 3/0041* (2013.01); *A61B 3/12* (2013.01); *G06T 3/60* (2013.01); *G06T 2207/10101* (2013.01)

(58) Field of Classification Search
CPC ............ G06T 3/60; G06T 2207/10101; G01N 21/4795; A61B 3/102; A61B 3/113; A61B 3/117; A61B 3/152; A61B 3/225; A61B 3/0025; A61B 3/0041; A61B 3/10; A61B 3/12

See application file for complete search history.

(56) References Cited

U.S. PATENT DOCUMENTS

| 2011/0102742 A1* | 5/2011 | Miyasa | .............. G01B 9/02068 351/206 |
| 2016/0089016 A1* | 3/2016 | Shibata | ................ A61B 3/1015 351/246 |
| 2018/0289257 A1* | 10/2018 | Ikegami | ............... A61B 3/1225 |

FOREIGN PATENT DOCUMENTS

WO   WO-2017135278 A1 *   8/2017   ............... A61B 3/10

* cited by examiner

*Primary Examiner* — Mustak Choudhury
(74) *Attorney, Agent, or Firm* — Xsensus LLP

(57) ABSTRACT

A new technique is provided to easily grasp the form of the fundus and the like of the eye to be examined being depicted in a tomographic image. An ophthalmic information processing device includes an image rotation circuit and a display control circuit. The image rotation circuit rotates a tomographic image of the eye to be examined acquired by using optical coherence tomography while making a measurement optical axis be eccentric relative to a predetermined site of the eye to be examined, in accordance with an eccentric amount and an eccentric direction of the measurement optical axis relative to the predetermined site. The display control circuit causes a display device to display the tomographic image rotated by the image rotation circuit.

14 Claims, 15 Drawing Sheets

OPHTHALMIC INFORMATION PROCESSING DEVICE, OPHTHALMIC DEVICE, OPHTHALMIC INFORMATION PROCESSING METHOD, AND PROGRAM

CROSS-REFERENCE TO RELATED APPLICATION

This application claims priority to Japanese Patent Application No. 2019-018738, filed Feb. 5, 2019, which is herein incorporated by reference in its entirety.

BACKGROUND

1. Technical Field

The present invention relates to ophthalmic information processing devices, ophthalmic devices, ophthalmic information processing methods, and programs.

2. Related Art

An ophthalmic device for screening, treating, or the like of an ophthalmic disease is required to be able to observe or capture the fundus or the like of an eye to be examined in a wide field of view in a simplified manner. As such an ophthalmic device, an optical coherence tomography meter, a scanning laser ophthalmoscope (hereinafter referred to as SLO), and the like are known. The SLO is a device configured to scan the fundus with light and detect the return light with a light-receiving device, thereby forming an image of the fundus.

Such various ophthalmic devices are proposed for observing the fundus or the like in a wide field of view.

For example, EP1308124 discloses a technique configured to acquire a wide angle image of an eye to be examined by causing a contact lens included in an objective lens system to make contact with the cornea of the eye to be examined. In addition, for example, U.S. Pat. No. 5,815,242 discloses a technique in which an anterior eye segment capturing system is provided in an ophthalmic device configured to acquire a wide angle image of an eye to be examined by using an ellipsoidal mirror so that the anterior eye segment capturing system captures the anterior eye segment of the eye to be examined.

SUMMARY

As a tomographic image of the eye to be examined and acquired by the optical coherence tomography meter becomes wider in terms of an angle of image, a physician or the like may more accurately make a diagnosis and the like. On the other hand, a physician or the like is required to make a diagnosis and the like while viewing a fundus image or the like significantly different from the shape of a fundus depicted in a tomographic image of the related art.

In nature, the form of the fundus or the like depicted in a tomographic image of the related art is different from the actual form. Therefore, physicians or the like may have an increased number of opportunities to view tomographic images in which forms unfamiliar with the observation of the related art are depicted.

The invention has been conceived in view of such circumstances, and an object thereof is to provide a new technique to make it possible to easily grasp the form of a fundus or the like of an eye to be examined being depicted in a tomographic image.

A first aspect of some embodiments is an ophthalmic information processing device including an image rotation circuit configured to rotate a tomographic image of an eye to be examined acquired by using optical coherence tomography while making a measurement optical axis be eccentric relative to a predetermined site of the eye to be examined in accordance with an eccentric amount and an eccentric direction of the measurement optical axis relative to the predetermined site; and a display control circuit configured to cause a display device to display the tomographic image rotated by the image rotation circuit.

A second aspect of some embodiments is such that, in the first aspect, the eccentric amount is determined by using at least one of a swing amount and a tilt amount of an optical system configured to perform the optical coherence tomography based on the eye to be examined, and the eccentric direction is determined by using at least one of a swing direction and a tilt direction of the optical system based on the eye to be examined.

A third aspect of some embodiments is such that, in the first aspect or the second aspect, the eccentric amount is determined by using a displacement amount of a projection position of fixation light flux relative to the measurement optical axis at a fundus of the eye to be examined, and the eccentric direction is determined by using a displacement direction of the projection position relative to the measurement optical axis at the fundus.

A fourth aspect of some embodiments further includes, in any one of the first to third aspects, a converting circuit configured to convert a pixel position of the tomographic image acquired by using the optical coherence tomography to a conversion position along an A-scan direction, and the image rotation circuit rotates the tomographic image in which the pixel position has been converted to the conversion position by the converting circuit.

A fifth aspect of some embodiments is such that, in any one of the first to fourth aspects, the display control circuit causes the display device to display the tomographic image rotated by the image rotation circuit in such a manner as to superimpose the tomographic image on an image representing a cross-sectional structure of the eye.

A sixth aspect of some embodiments is such that, in the fifth aspect, the display control circuit adjusts a size of the above-mentioned image based on the tomographic image, and causes the display device to display the tomographic image rotated by the image rotation circuit in such a manner as to superimpose the tomographic image on the image having the adjusted size.

A seventh aspect of some embodiments is an ophthalmic device including an optical coherence tomography (OCT) sensor configured to acquire a tomographic image of the eye to be examined by using optical coherence tomography while making a measurement optical axis be eccentric relative to a predetermined site of the eye to be examined, and the ophthalmic information processing device described in any one of the above aspects.

An eighth aspect of some embodiments further includes, in the seventh aspect, a swing mechanism configured to move an optical system for performing the optical coherence tomography in a horizontal direction based on the eye to be examined, and the swing mechanism causes the measurement optical axis to be eccentric relative to a predetermined site of the eye to be examined.

A ninth aspect of some embodiments further includes, in the seventh or eighth aspect, a tilt mechanism configured to move the optical system for performing the optical coherence tomography in a vertical direction based on the eye to be examined, and the tilt mechanism causes the measurement optical axis to be eccentric relative to a predetermined site of the eye to be examined.

A tenth aspect of some embodiments further includes, in any one of the seventh to ninth aspects, a fixation optical system configured to project fixation light flux onto a projection position that is changeable relative to the fundus of the eye to be examined.

An eleventh aspect of some embodiments is an ophthalmic information processing method including image-rotating a tomographic image of an eye to be examined acquired by using optical coherence tomography while making a measurement optical axis be eccentric relative to a predetermined site of the eye to be examined in accordance with an eccentric amount and an eccentric direction of the measurement optical axis relative to the predetermined site; and display-controlling to cause a display device to display the tomographic image rotated by the image-rotating.

A twelfth aspect of some embodiments is such that, in the eleventh aspect, the eccentric amount is determined by using at least one of a swing amount and a tilt amount of an optical system configured to perform the optical coherence tomography based on the eye to be examined, and the eccentric direction is determined by using at least one of a swing direction and a tilt direction of the optical system based on the eye to be examined.

A thirteenth aspect of some embodiments is such that, in the eleventh or twelfth aspect, the eccentric amount is determined by using a displacement amount of a projection position of fixation light flux relative to the measurement optical axis at a fundus of the eye to be examined, and the eccentric direction is determined by using a displacement direction of the projection position relative to the measurement optical axis at the fundus.

A fourteenth aspect of some embodiments is such that, in any one of the eleventh to thirteenth aspects, the display-controlling causes the display device to display the tomographic image rotated by the image-rotating in such a manner as to superimpose the tomographic image on an image representing a cross-sectional structure of the eye.

A fifteenth aspect of some embodiments is a program configured to cause a computer to execute the image-rotating and the display-controlling of the ophthalmic information processing method described in any one of the above-discussed aspects.

Note that the configurations according to the plurality of aspects described above may be combined as desired.

According to the aspects of the invention, it is possible to provide a new technique by which the form of the fundus or the like of the eye to be examined being depicted in a tomographic image is easily grasped.

DESCRIPTION OF EMBODIMENTS

Figure 1:
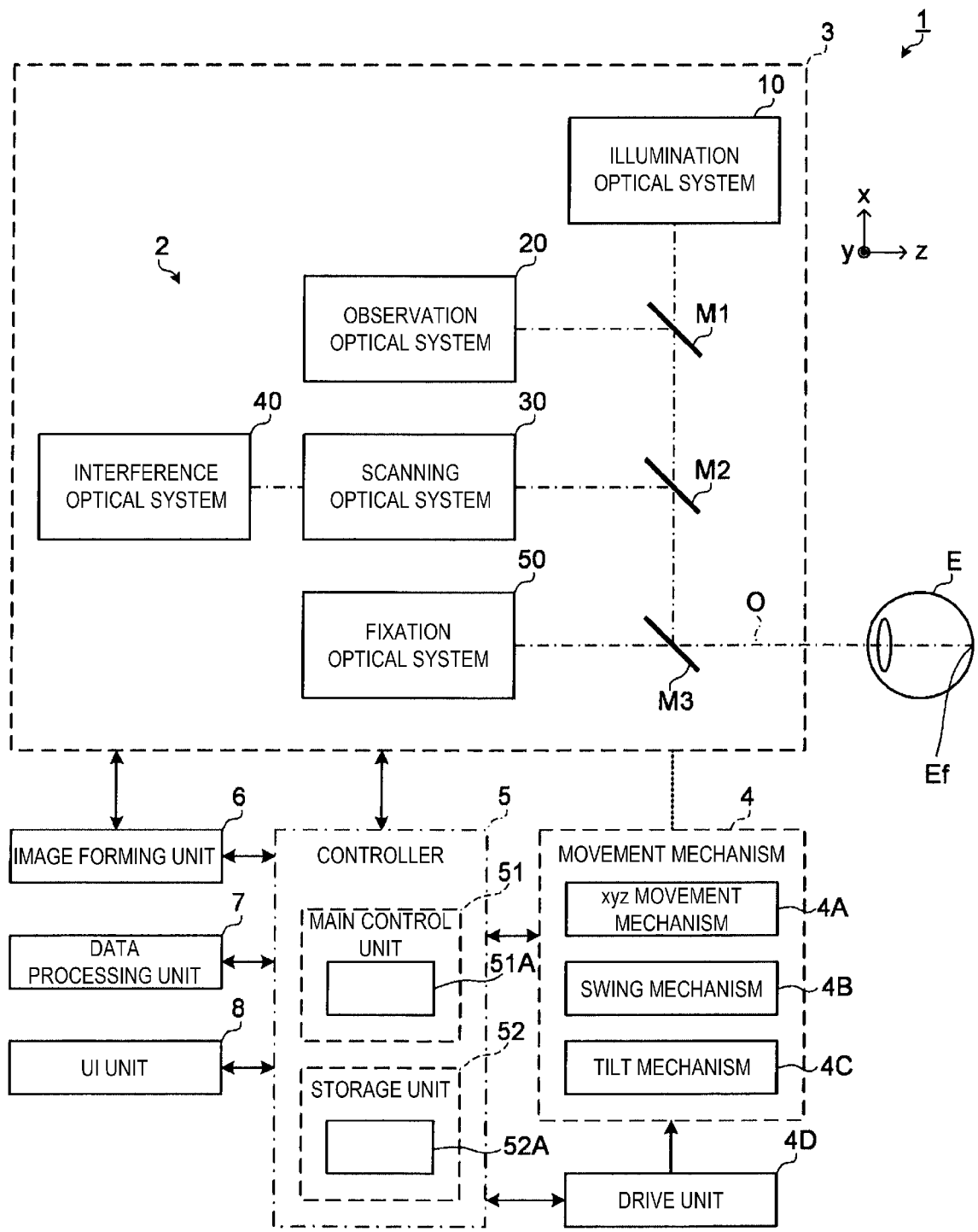
FIG. 1 is a schematic diagram illustrating an example of a configuration of an ophthalmic device according to an embodiment.

Examples of embodiments of ophthalmic information processing devices, ophthalmic devices, ophthalmic information processing methods, and programs according to the aspects of the invention will be described in detail with reference to the drawings. The contents of description of the documents cited in this specification, any known technology, and the like may be quoted in the following embodiments.

An ophthalmic information processing device according to an embodiment rotates a tomographic image of an eye to be examined acquired by using optical coherence tomography (OCT) while making a measurement optical axis be eccentric relative to a predetermined site (for example, a fovea or macular region) of the eye to be examined. The ophthalmic information processing device rotates the tomographic image about a predetermined reference position in the tomographic image in accordance with an eccentric amount and an eccentric direction of the measurement optical axis relative to the predetermined site. The ophthalmic information processing device causes a display device to display the tomographic image rotated in accordance with the eccentric amount and the eccentric direction. For example, the tomographic image is rotated in such a manner that a predetermined site is arranged at a predetermined position. As a result, it is easy to grasp an OCT measurement position based on the predetermined site.

In some embodiments, the ophthalmic information processing device corrects a tomographic image so that the shape of a fundus or the like takes the actual shape by converting a pixel position of the acquired tomographic image to a conversion position along an A-scan direction, and rotates the corrected tomographic image. As a result, even in a case where an unfamiliar tomographic image is displayed on a display device, it is possible to easily grasp the OCT measurement position. By using the corrected tomographic image (or scan data), it is possible to acquire information of the form representing the form of the eye to be examined as information representing the actual form.

An ophthalmic information processing method according to an embodiment includes one or more pieces of processing to achieve processes executed by a processor (computer) in the ophthalmic information processing device according to the embodiment. A program according to an embodiment causes the processor to execute each processing of the ophthalmic information processing method according to the embodiment.

Herein, "processor" refers to a circuit such as a central processing unit (CPU), a graphics processing unit (GPU), an application specific integrated circuit (ASIC), or a programmable logic device (for example, a simple programmable logic device (SPLD), a complex programmable logic device (CPLD), or a field programmable gate array (FPGA)). The processor enables the functions according to the embodiment by reading out and executing the program stored in a storage circuit or a storage device, for example.

Images acquired by OCT may be collectively referred to herein as OCT images. Measuring operation for forming OCT images may be referred to as OCT measurement.

The following describes a case where the ophthalmic device according to the embodiment has a function of the ophthalmic information processing device according to the embodiment. However, the ophthalmic information processing device according to the embodiment may be configured to acquire a tomographic image or the like from an external ophthalmic device.

The ophthalmic device according to the embodiment is able to scan an anterior or posterior eye segment with a light beam to acquire distribution of predetermined data (for example, images, layer thickness distribution, lesion distribution). Examples of such an ophthalmic device include an optical coherence tomography meter and an SLO. In the following, a case where the ophthalmic device has a function of the light coherence tomography meter will be described.

The ophthalmic device according to the embodiment is able to scan a posterior eye segment over a wide angle by the measuring (capturing) while making the measurement optical axis be eccentric relative to a position of the fovea (or macular region) of the eye to be examined. In some embodiments, the ophthalmic device includes a swing mechanism configured to move an optical system in a horizontal direction based on the eye to be examined, and scans the posterior eye segment over a wide angle by moving the optical system in the horizontal direction. In some embodiments, the ophthalmic device includes a tilt mechanism configured to move the optical system in a vertical direction based on the eye to be examined, and scans the posterior eye segment over a wide angle by moving the optical system in the vertical direction. In some embodiments, the ophthalmic device includes both the swing mechanism and the tilt mechanism. In some embodiments, the ophthalmic device includes a fixation optical system configured to project fixation light flux onto the fundus of the eye to be examined, and scans the posterior eye segment over a wide angle by changing the projection position of the fixation light flux at the fundus. For the fixation light flux, an internal fixation optical system or an external fixation optical system may be used.

Hereinafter, a case in which the ophthalmic device according to the embodiment includes the swing mechanism, the tilt mechanism, and the fixation optical system will be described. However, the ophthalmic device according to the embodiment may have a configuration in which at least one of the swing mechanism, the tilt mechanism, and the fixation optical system is omitted.

Hereinafter, unless otherwise stated, the left and right direction is referred to as an x-direction, the up and down direction is referred to as a y-direction, and the front and rear direction (depth direction) is referred to as a z-direction, when viewed form a subject to be examined. The x-, y-, and z-directions define a three-dimensional orthogonal coordinate system.

Configuration

FIG. 1 illustrates a schematic configuration of an ophthalmic device according to the embodiment. An ophthalmic device 1 according to the embodiment collects data by scanning a fundus Ef of an eye to be examined E with light, and acquires an image of the fundus Ef based on the collected data. In FIG. 1, a tomographic image, a three-dimensional image, a front image, and the like of the fundus Ef are acquired.

The ophthalmic device 1 includes an optical system 2, a housing section 3 configured to house the optical system 2, a movement mechanism 4, a controller 5, an image forming unit 6, a data processing unit 7, and a user interface (UI) unit 8. The ophthalmic device 1 may be provided with a drive unit 4D configured to drive the movement mechanism 4 under control of the controller 5.

Movement Mechanism

The movement mechanism 4 moves the optical system 2 (housing section 3). The movement mechanism 4 includes an xyz movement mechanism 4A, a swing mechanism 4B, and a tilt mechanism 4C. The xyz movement mechanism 4A moves the optical system 2 in the x-, y-, and z-directions. The swing mechanism 4B revolves (turns) the optical system 2 in the horizontal direction based on a predetermined position (for example, a pupil position) of the eye to be examined E. Specifically, the swing mechanism 4B moves the optical system 2 in the horizontal direction along an arc-shaped trajectory. The swing mechanism 4B revolves the optical system 2 within a predetermined angle range of movement. The tilt mechanism 4C revolves (turns) the optical system 2 in the vertical direction based on the predetermined position (for example, the pupil position) of the eye to be examined E. Specifically, the tilt mechanism 4C moves the optical system 2 in the vertical direction along an arc-shaped trajectory. The tilt mechanism 4C revolves the optical system 2 within a predetermined angle range of movement. The revolution center is not limited to the pupil position, and may be a position displaced from the pupil position within a range that does not obstruct the scanning of the posterior eye segment. The position within such a range is referred to as a "nearby position of the pupil position". The displacement of the nearby position relative to the pupil position may be displacement in any direction in the xyz space. Hereinafter, "pupil position" means a "pupil position or a nearby position thereof", unless otherwise noted.

The xyz movement mechanism 4A is used for positioning (alignment) and tracking of the optical system 2 with respect to the eye to be examined E, for example. The tracking is an operation to move the optical system 2 in response to the movement of the eye to be examined E. When the tracking is to be performed, alignment and focusing are performed in advance. The tracking is a function of maintaining a preferred positional relationship in which the alignment and focusing are achieved by moving the optical system 2 in real time in response to the position, orientation, and the like of the eye to be examined E based on the image obtained by capturing (video capturing) the eye to be examined E.

The swing mechanism 4B and the tilt mechanism 4C are used for a wide range scanning with respect to the eye to be examined E (fundus Ef), capturing an image of the peripheral portion of the fundus Ef, and the like. The swinging mechanism 4B and the tilt mechanism 4C revolve the optical system 2 three-dimensionally within a predetermined angle range of movement about the pupil position, for example.

The above-mentioned movement mechanism 4 includes, for example, one or more holding members configured to hold the optical system 2, and one or more guide arms movably provided at any position within the angle range of movement. The movement mechanism 4 slides along the guide arm. The number of dimensions for the revolution direction is not limited to three, and may be, for example, one or two.

The drive unit 4D operates under the control of the controller 5, for example. In this case, the drive unit 4D includes an actuator (not illustrated) configured to generate a driving force for revolving the optical system 2. The actuator generates the driving force in response to a control signal from the controller 5. The driving force is transmitted by a transmission mechanism (not illustrated) to move the holding member along the guide arm. With the above control, the optical system 2 is revolved in a direction corresponding to the control signal by an angle corresponding to the control signal. In this case, the position of the optical system 2 is identified by the contents of control on the drive unit 4D by the controller 5. The identified position information (movement information) is used, for example, by the controller 5, image forming unit 6, data processing unit 7, and the like.

Note that the movement mechanism 4 does not have to include an actuator. In this case, the optical system 2 is manually revolved. The position of the optical system 2 is detected by an encoder, a position sensor, or the like. The position information acquired in this manner is used by, for example, the controller 5, image forming unit 6, data processing unit 7, and the like.

In some embodiments, the movement mechanism 4 moves the optical system 2 by moving the housing section 3. In some embodiments, the movement mechanism 4 only moves part of the optical system 2.

Optical System

The optical system 2 includes an optical member, a mechanism, and the like for optically collecting data of the fundus Ef. The optical system 2 includes an illumination optical system 10, an observation optical system 20, a scanning optical system 30, an interference optical system 40, and a fixation optical system 50. In some embodiments, the optical system 2 includes at least one of an alignment system for aligning the optical system 2 with respect to the eye to be examined E and a focus system for focusing the optical system 2 with respect to the eye to be examined E.

The optical system 2 includes an optical element as a light path coupling and decoupling member for decoupling a light path of the above-described optical system and coupling the light path with another optical system. In FIG. 1, beam splitters M1 to M3 are provided as light path coupling and decoupling members, for example.

The beam splitter M1 couples the light path of the illumination optical system 10 and the light path of the observation optical system 20, decouples the light path of the observation optical system 20 from a light path of the light having passed through the beam splitter M2, and the like.

The beam splitter M1 has a property that transmits the light from the illumination optical system 10 and reflects the light having passed through the beam splitter M2 toward the observation optical system 20. It is desirable for the beam splitter M1 to couple the optical systems in such a manner that an optical axis of the illumination optical system 10 and an optical axis of the observation optical system 20 become substantially coaxial.

The beam splitter M2 couples the light path of the scanning optical system 30 (or the interference optical system 40) and the light path of the illumination optical system 10 (or the observation optical system 20), decouples the light path of the scanning optical system 30 (or the interference optical system 40) and the light path of the illumination optical system 10 (or the observation optical system 20) from a light path of the light reflected by the beam splitter M3, and the like. The beam splitter M2 has a property that transmits the light from the beam splitter M1, reflects the light from the scanning optical system 30 toward the beam splitter M3, reflects, toward the scanning optical system 30, return light from the eye to be examined E of the light from the scanning optical system 30, and transmits the return light from the eye to be examined E of the light from the illumination optical system 10. It is desirable for the beam splitter M2 to couple the optical systems in such a manner that an optical axis of the scanning optical system 30 (or the interference optical system 40) and the optical axis of the illumination optical system 10 (or the observation optical system 20) become substantially coaxial.

The beam splitter M3 couples the light path of the fixation optical system 50 with the light paths of the optical systems other than that. The beam splitter M3 has a property that transmits the light from the fixation optical system 50, and reflects the light from the optical systems other than that (such as the illumination optical system 10 and the interference optical system 40) or the return light thereof. It is desirable for the beam splitter M3 to couple the optical systems in such a manner that an optical axis of the fixation optical system 50 and the optical axes of the optical systems other than that become substantially coaxial.

Although not illustrated in FIG. 1, an objective lens is disposed between the beam splitter M3 and the eye to be examined E.

Illumination Optical System

The illumination optical system 10 illuminates the anterior eye segment of the eye to be examined E. The illumination optical system 10 includes an illumination light source, a lens, and the like.

Observation Optical System

The observation optical system 20 is used to observe the anterior eye segment of the eye to be examined E being illuminated by the illumination optical system 10. The observation optical system 20 includes at least one of an eyepiece and an imaging element. The eyepiece is used for naked-eye observation of the eye to be examined E. The imaging element is used to acquire a front image of the eye to be examined E.

Illumination light from the illumination optical system 10 passes through the beam splitters M1 and M2, is reflected by the beam splitter M3, passes through an objective lens (not illustrated), and illuminates the anterior eye segment of the eye to be examined E. Return light of the illumination light from the eye to be examined E travels in the same path in the reverse direction, and is reflected by the beam splitter M1 to be incident on the observation optical system 20. The return light incident on the observation optical system 20 is focused on an imaging face of the imaging element, for example. An image acquired by using the imaging element is displayed on a display device (not illustrated) by the controller 5 controlling the UI unit 8 when the controller 5 has received a signal from the imaging element.

Scanning Optical System

The scanning optical system 30 deflects the measurement light outputted from the interference optical system 40, under the control of the controller 5. For example, the scanning optical system 30 deflects the light within a two-dimensional angle range of deflection. The number of dimensions for the deflection direction is not limited to two, and may be one, for example.

The scanning optical system 30 includes an optical scanner. A deflection member with a single axis or a deflection member with two axes orthogonal to each other is used as the optical scanner. Examples of the deflection member include a galvano-mirror, polygon mirror, rotatable mirror, Dove prism, double-Dove prism, rotation prism, and MEMS mirror scanner. In a case where a deflection member with two axes is used, a deflection member for high speed scanning (for example, a polygon mirror) and a deflection member for slow speed scanning (for example, a galvano-mirror) may be combined. The scanning optical system 30 may further include an optical element for projecting the deflected light onto the fundus Ef.

The optical scanner is disposed at or near an optically substantially conjugate position with respect to the pupil of the eye to be examined E. With this, the pupil of the eye to be examined E (or a position near the pupil) is taken as a scanning center position, and the interior of the eye to be examined E is scanned with the measurement light deflected about the scanning center position.

Interference Optical System

The interference optical system 40 splits the light from the light source into measurement light and reference light, radiates the measurement light onto the eye to be examined E (fundus Ef), and guides, to a detector, interference light obtained by superimposing the reference light and the return light of the measurement light from the eye to be examined E. To the interference optical system 40, the optical coherence tomography (OCT) of, for example, a swept source type or a spectral domain type is applied.

When the OCT of the swept source type is applied, the interference optical system 40 includes an OCT light source, which is a wavelength sweep type (wavelength scan type) light source capable of sweeping (scanning) the wavelength of emitted light. As the wavelength sweep type light source, for example, a laser light source that includes a resonator and emits light having a predetermined center wavelength is used. The wavelength sweep type light source changes the output wavelength in terms of time in the near infrared wavelength band that is not visible to the human eye.

The light outputted from the OCT light source may be, for example, near infrared light having a center wavelength of approximately 1040 to 1060 nm (for example, 1050 nm) and having a wavelength width of approximately 50 nm. The swept source type is particularly described in this embodiment; however, in the case where the spectral domain type is applied, a light output device such as a super luminescent diode (SLD), an LED, or a semiconductor optical amplifier (SOA) is used as the light source. In general, the configuration for the OCT light source is appropriately selected depending on the type of OCT.

The light outputted from the OCT light source is guided to a fiber coupler by the optical fiber to be divided into measurement light and reference light. The measurement light is guided by the optical fiber, emitted from the fiber end portion, and is made to be parallel light flux by a collimating lens. The fiber end portion of the optical fiber is disposed at or near a fundus conjugate position which is an optically substantially conjugate position with respect to the fundus Ef of the eye to be examined E. The measurement light is deflected by the scanning optical system 30, reflected by the beam splitter M2, and reflected by the beam splitter M3 toward the eye to be examined E. The measurement light radiated onto the fundus Ef is scattered and reflected at a measurement site such as the fundus Ef, for example. The scattered light and reflected light may be collectively referred to as return light of the measurement light. The return light of the measurement light travels in the same path in the reverse direction to be guided to the fiber coupler described above.

On the other hand, the reference light is guided by the optical fiber to be reflected by a reference mirror movable along the light path of the reference light, and the reflected light is guided to the fiber coupler again. In the light path of the reference light, there may be provided a polarization controller (polarization regulator), an optical element for dispersion compensation (such as pair prism), an optical element for polarization correction (such as a wavelength plate), an optical attenuator (attenuator) configured to adjust, under the control of the controller 5, the light amount of the reference light passing through the optical fiber, and the like. The polarization controller adjusts a polarization state of the reference light passing through the optical fiber formed in a loop shape, by applying stress to the optical fiber from the outside.

A light path length changing unit is provided in at least one of the light path of the reference light and the light path of the measurement light. The light path length changing unit relatively changes the light path length of the measurement light with respect to the light path length of the reference light. The change of the light path length is used for correction of a light path length corresponding to the axial length, interference state adjustment, and the like. The above-mentioned light path length changing unit includes, for example, a corner cube and a mechanism that receives a command from the controller 5 to move the corner cube along a light path of the incident light.

The above-mentioned fiber coupler, into which the return light of the measurement light and the reference light reflected by the reference mirror enter, combines the return light of the measurement light and the reference light. The interference light generated by the above light combination is guided by the optical fiber to the detector. At this time, the interference light is split by another fiber coupler at a predetermined branching ratio (for example, 1:1), so that a pair of pieces of interference light is generated. The pair of pieces of interference light is detected by a detector (balanced photodiode). In the case of the spectral domain OCT, the detector (spectrometer) breaks down the interference light generated by the fiber coupler into a plurality of wavelength components and detects them.

The detector sends a detection result (detection signal) of the pair of pieces of interference light to a data acquisition system (DAQ) (not illustrated). A clock is supplied to the DAQ from the OCT light source. The clock is generated in synchronization with the output timing of each wavelength that is swept within a predetermined wavelength range by a wavelength variable light source. The DAQ samples the detection signal based on the clock. The sampling result is sent to the image forming unit 6 to form an OCT image.

Fixation Optical System

The fixation optical system 50 projects fixation light flux onto the fundus Ef of the eye to be examined E. The fixation optical system 50 is controlled by the controller 5, and is configured such that the projection position of the fixation light flux is changeable at the fundus Ef of the eye to be examined E. As a result, it is possible to indicate a fixation target at a position eccentric relative to the measurement optical axis.

The above-discussed fixation optical system 50 includes a display device such as a liquid crystal display configured to display a target pattern in response to a command from the controller 5. The display device is able to change the projection position of the fixation light flux at the fundus Ef by changing the display position of the target pattern. In some embodiments, the fixation optical system 50 includes a plurality of fixation light sources, and selectively turns on the plurality of fixation light sources in response to a command from the controller 5. In this case, the fixation optical system 50 is able to change the projection position of the fixation light flux at the fundus Ef by changing the fixation light source to be turned on among the plurality of fixation light sources. Each of the plurality of fixation light sources is a visible light source configured to output visible light. In some embodiments, the ophthalmic device 1 may be provided with a plurality of external fixation light sources. The plurality of external fixation light sources are able to project fixation light onto a fellow eye of the eye to be examined E. The projection position of the fixation light at the fellow eye may be changed. By changing the projection position of the fixation light with respect to the fellow eye, it is possible to change the fixation position of the eye to be examined E. For example, a movable fixation target may be generated by selectively turning on the plurality of external fixation light sources. In some embodiments, a movable fixation target is generated by one or more external fixation light sources that are movable.

As described above, an alignment system, a focus system, or the like may be provided in the optical system 2. The alignment system or focus system also includes, as in the related art, an optical system for projecting an indicator (alignment indicator, focusing indicator) onto the eye to be examined E, and an optical system for detecting return light thereof. It is also possible to have a configuration in which two or more imaging devices configured to capture the anterior eye segment of the eye to be examined E are provided, and alignment is performed by analyzing (for example, using a triangular method) two or more anterior eye segment images acquired by the imaging devices at substantially the same time.

Scanning

In the optical system 2, for example, the measurement light generated from the OCT light source in the interference optical system 40 is deflected by the scanning optical system 30 and imaged as spot light on the fundus Ef through the pupil of the eye to be examined E. The return light thereof is the light that returns from the projection position (and a position near the projection position) of the spot light to the optical system 2. The return light is guided to the fiber coupler as described above and is combined with the reference light. The interference light of the reference light and the return light of the measurement light is detected by the detector. The detector generates an electrical signal (light-receiving signal) by photoelectric conversion. Note that the projection position of the spot light may be described as a spot position.

This series of processes corresponds to measurement of one point of the fundus Ef. The scanning optical system 30 moves the spot position within a predetermined angle range of deflection. That is, the scanning within the predetermined angle range of deflection is achieved by the scanning optical system 30. The movement mechanism 4 revolves the optical system 2 within a predetermined angle range of movement. That is, the movement mechanism 4 moves a scan area (single scan area) corresponding to the deflection angle range of the scanning optical system 30. By combining these, a wide range of fundus Ef may be measured while moving a single scan area.

Figure 2:
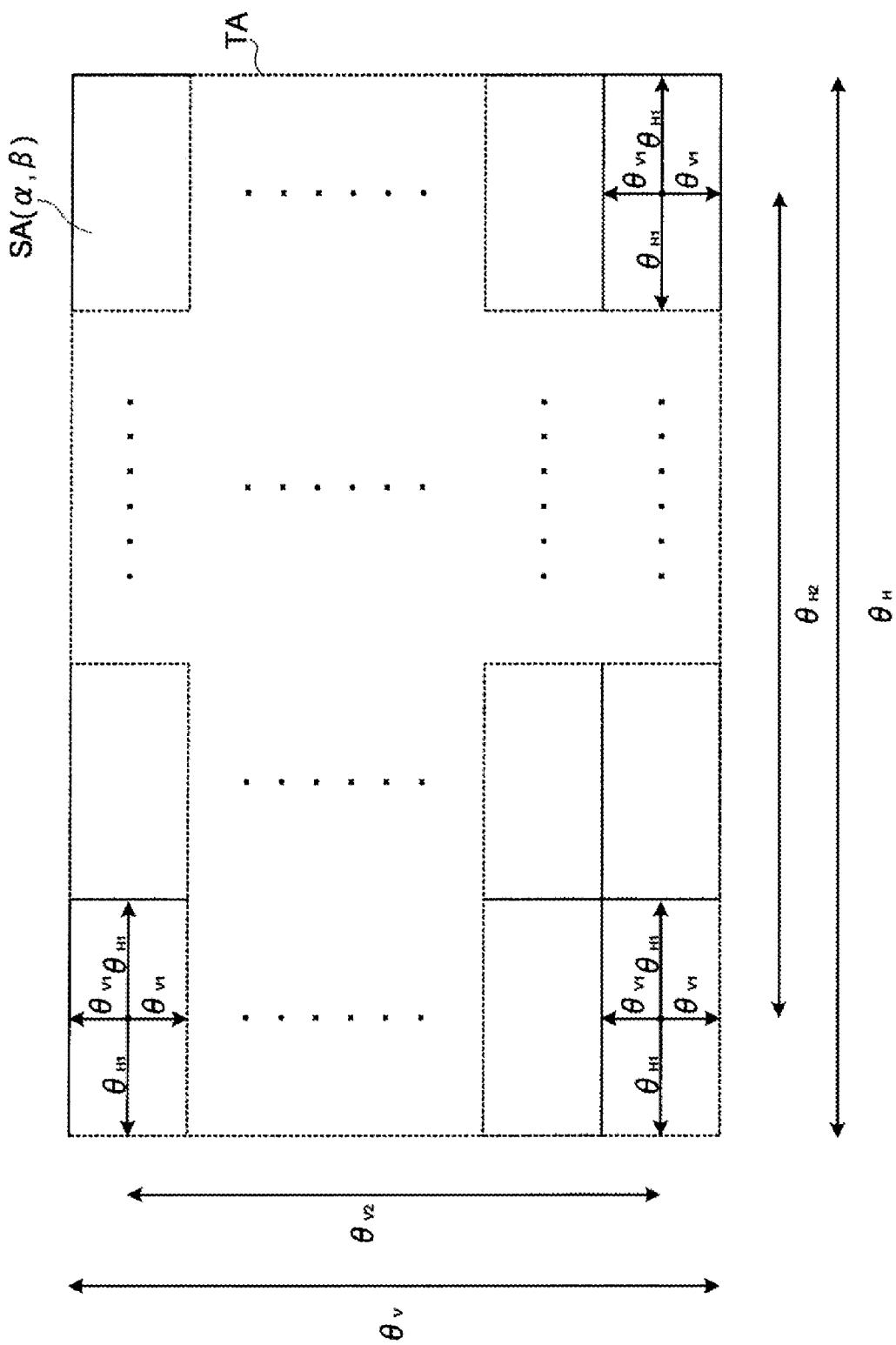
FIG. 2 is a schematic diagram for describing a process performed by an ophthalmic device according to an embodiment.

FIG. 2 illustrates a descriptive diagram of a scanning operation by the ophthalmic device 1 according to the embodiment.

As illustrated in FIG. 2, an entire scan area TA includes at least one sub-scan area SA ($\alpha$, $\beta$). The extent in the horizontal direction (for example, the x-direction) of the entire scan area TA is defined as $\theta H$, and the extent in the vertical direction (for example, the y-direction) is defined as $\theta V$. The entire scan area TA is divided into a plurality of sub-scan areas SA ($\alpha$, $\beta$) arranged in matrix form. Here, $\alpha$=1, 2, . . . , J, and $\beta$=1, 2, . . . , K, where J and K are each an integer of 1 or greater, and at least one of J and K is an integer of 2 or greater. Not all of the plurality of sub-scan areas SA ($\alpha$, $\beta$) are required to have the same size, and not all thereof are required to have the same shape.

Each sub-scan area SA ($\alpha$, $\beta$) corresponds to a single scan area. Part of the sub-scan area SA ($\alpha$, $\beta$) and part of the sub-scan area SA ($\alpha$+1, $\beta$) may overlap each other, and part of the sub-scan area SA ($\alpha$, $\beta$) and part of the sub-scan area SA ($\alpha$, $\beta$+1) may overlap each other.

In the embodiment, the scanning of the entire scan area TA is achieved by sequentially scanning the plurality of sub-scan areas SA ($\alpha$, $\beta$). The scanning of each sub-scan area SA (a, R) is performed by controlling the scanning optical system 30, and the sub-scan area SA ($\alpha$, $\beta$) to be scanned is switched by the control of the movement mechanism 4.

The scanning of each sub-scan area SA ($\alpha$, $\beta$) will be described below. For example, the scanning optical system 30 deflects measurement light from the interference optical system 40 within a predetermined deflection angle range. The extent in the horizontal direction of the deflection angle range is referred to as "$2 \cdot \theta H1$", and the extent in the vertical direction thereof is referred to as "$2 \cdot \theta V1$". That is, the scanning optical system 30 is able to move the spot position by "$\theta H1$" each in the left and right direction based on the deflection center thereof (for example, a position on the optical axis of the scanning optical system 30), and able to move the spot position in the up and down direction by "$\theta V1$" each. Since the deflection angle and a distance in the xy plane (length of the arc) correspond to each other, they may be identified with each other.

The sub-scan area SA ($\alpha$, $\beta$) is switched by revolving the optical system 2 within a predetermined angle range of movement about the pupil position by using the movement mechanism 4. The extent in the horizontal direction of the movement angle range is referred to as "$\theta H2$", and the extent in the vertical direction thereof is referred to as "$\theta V2$". That is, the movement mechanism 4 is able to revolve the optical system 2 in the horizontal direction by "$\theta H2$", and able to revolve the optical system 2 in the vertical direction by "$\theta V2$".

According to the above-discussed scanning optical system 30 and movement mechanism 4, in the case where the plurality of sub-scan areas SA ($\alpha$, $\beta$) are arranged without overlapping each other and without any gap therebetween, the movement range in the horizontal direction of the spot position is expressed as $\theta H = \theta H2 + 2 \times \theta H1$, and the movement range in the vertical direction thereof is expressed as $\theta V = \theta V2 + 2 \times \theta V1$. The area with the extent in the horizontal direction being θH and the extent in the vertical direction being θV corresponds to the entire scan area TA. In the case where overlaps or gaps are provided, the entire scan area TA is determined depending on widths of the overlaps or intervals between the gaps.

As one example, the following settings are made: θH1=60 degrees, θH2=40 degrees, θV1=40 degrees, and θV2=40 degrees. This makes it possible to scan a range of 160 degrees in the horizontal direction and 120 degrees in the vertical direction. Note that θH1, θH2, θV1, and θV2 are determined taking into account any factors such as a cost and an operation distance.

Controller

The controller 5 controls constituent elements of the device. The controller 5 includes a processor and a storage device (storage circuit). A computer program for controlling the ophthalmic device 1 is stored beforehand in the storage device. The computer program includes a light source control program, a scanning control program, a movement mechanism control program, an image forming control program, a data processing control program, a user interface control program, and the like. By the processor operating in accordance with such a computer program, the controller 5 carries out control processing.

The controller 5 includes a main control unit 51 and a storage unit 52.

Main Control Unit

The main control unit 51 includes a processor and controls constituent elements of the ophthalmic device 1. For example, the main control unit 51 controls the optical system 2, the movement mechanism 4 (drive unit 4D), the image forming unit 6, the data processing unit 7, the UI unit 8, and the like.

Control over the optical system 2 includes control of a focusing drive unit configured to move a focusing lens (not illustrated), control of an imaging element such as an image sensor, control of the optical scanner, control of the light path length changing unit, control of the optical attenuator, control of the polarization controller, control of the fixation optical system 50 (display device), and the like. In some embodiments, the focusing lens is disposed between the scanning optical system 30 and the beam splitter M2. In some embodiments, the focusing lens is included in the observation optical system 20.

Control over the movement mechanism 4 includes control of a drive unit configured to drive the xyz movement mechanism 4A, control of a drive unit configured to drive the swing mechanism 4B, control of a drive unit configured to drive the tilt mechanism 4C, and the like.

In a case of manual alignment, the optical system and the eye to be examined E are moved relatively to each other by the user operating with respect to the UI unit 8, which will be described later, in such a manner that the displacement of the eye to be examined E with respect to the optical system is canceled. For example, the main control unit 51 controls the xyz movement mechanism 4A to move the optical system 2 and the eye to be examined E relatively to each other by outputting, to the xyz movement mechanism 4A (drive unit 4D), a control signal corresponding to the content of the operation with respect to the UI unit 8.

In a case of auto-alignment, the optical system and the eye to be examined E are moved relatively to each other by the main control unit 51 controlling the xyz movement mechanism 4A in such a manner that the displacement of the eye to be examined E with respect to the optical system is canceled. In some embodiments, the main control unit 51 controls the xyz movement mechanism 4A to move the optical system 2 and the eye to be examined E relatively to each other by outputting a control signal to the xyz movement mechanism 4A (drive unit 4D) in such a manner that a measurement optical axis O of the optical system 2 substantially matches the axis of the eye to be examined E and a distance of the optical system with respect to the eye to be examined E takes a predetermined operation distance. The operation distance is a predefined value, which is also referred to as a working distance of the objective lens (not illustrated), and corresponds to a distance between the eye to be examined E and the optical system 2 at the time of measurement (at the time of image capturing) using the optical system.

By coordinatedly controlling the scanning optical system 30 and the movement mechanism 4, scanning as exemplified in FIG. 2 may be achieved. For example, a predefined deflection pattern for deflecting the measurement light and a predefined movement pattern for moving the optical system 2 are stored beforehand in the storage device (storage unit 52) of the main control unit 51. The deflection pattern and the movement pattern may take default settings or may be set by a user. Further, a configuration may be employed in which a plurality of deflection patterns and a plurality of movement patterns are combined as desired and applied. The selection of the patterns is made by, for example, the user or the main control unit 51.

The main control unit 51 coordinately performs the control (scanning control) of the scanning optical system 30 based on the deflection pattern and the control (movement control) of the movement mechanism 4 based on the movement pattern. For example, the main control unit 51 alternately performs the scanning control and the movement control. Here, a single scanning control corresponds to scanning of a single scan area (one sub-scan area), and a single movement control corresponds to switching of a sub-scan area. As another example, the main control unit 51 is able to perform the scanning control and movement control in parallel in at least some phases of the scanning with respect to the entire scan area.

Figure 3:
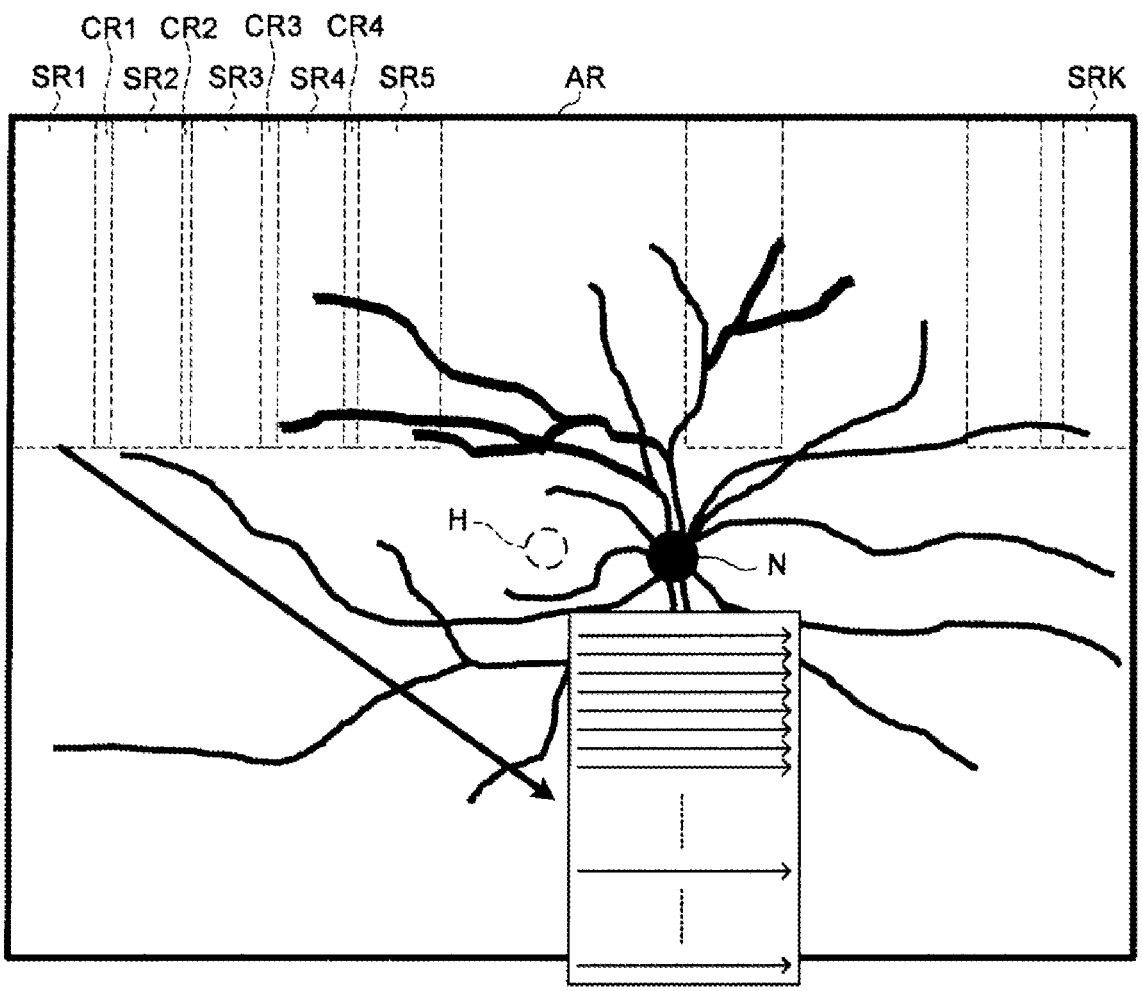
FIG. 3 is a schematic diagram for describing a process performed by an ophthalmic device according to an embodiment.

FIG. 3 illustrates a descriptive diagram of a scan mode according to the embodiment. FIG. 3 schematically depicts an aspect in which an entire scan area AR including an optic papilla N and a macular region H is divided into a plurality of sub-scan areas and scanned.

By controlling the movement mechanism 4 in accordance with the predefined movement pattern, the main control unit 51 moves a sub-scan area (single scan area) to be scanned in the order of, for example, sub-scan areas SR1, SR2, SR3, and the like. At this time, adjacent sub-scan areas SRi and SR (i+1) have an overlapping area CRi (i=1, 2, 3, . . . ). When forming an image of the entire scan area AR from a plurality of images obtained from the plurality of sub-scan areas, it is possible to perform positioning of the adjacent images by making use of the overlapping areas. The main control unit 51 controls the optical system 2 to scan each of the sub-scan areas based on the predefined deflection pattern. In the example illustrated in FIG. 3, a raster scan is applied. Other examples of the deflection pattern include a circle scan, concentric circular scan, radial scan, and slit scan (one-dimensional scan).

The main control unit 51 is able to perform a plurality of preliminary operations before performing OCT measurement. The preliminary operations include alignment, focus roughness adjustment, polarization adjustment, focus fine adjustment, and the like. The plurality of preliminary operations are performed in a predetermined order. In some embodiments, the plurality of preliminary operations are performed in the order described above.

The focus roughness adjustment is focus adjustment using a split indicator. The focus roughness adjustment may also be performed by determining the position of the focusing lens, based on the information in which eye refractive power acquired in advance and a position of the focusing lens provided in the observation optical system 20 are associated with each other, and a measurement value of the refractive power of the eye to be examined E.

The focus fine adjustment is performed based on interference sensitivity of the OCT measurement. For example, by monitoring the interference strength (interference sensitivity) of an interference signal acquired by the OCT measurement of the eye to be examined E, it is possible to perform the focus fine adjustment by finding the position of the focusing lens (the focusing lens provided between the scanning optical system 30 and the beam splitter M2) that brings the maximum interference strength, and moving the focusing lens to that position.

In light path length difference adjustment, a predetermined position in the eye to be examined E is controlled to be a reference position of a measurement range in the depth direction. This control is performed on the light path length changing unit described above. With this, a light path length difference between the measurement light path and the reference light path is adjusted. By setting the reference position by the light path length difference adjustment, the OCT measurement may be precisely performed with respect to the desired measurement range in the depth direction simply by changing a wavelength sweep speed.

In the polarization adjustment, the polarization state of the reference light is adjusted to optimize the interference efficiency of the measurement light and the reference light.

The main control unit 51 includes a display control unit 51A. The display control unit 51A controls a display device (display unit) of the UI unit 8 or an external display device (not illustrated) to display various pieces of information. The information caused to be displayed by the display control unit 51A includes information representing the state of the optical system 2, information representing the state of the movement mechanism 4, information representing the control content or control result of the controller 5, an image formed by the image forming unit 6, a processing result by the data processing unit 7, information for assisting the operation with respect to an operation device of the UI unit 8, and the like.

Storage Unit

The storage unit 52 stores various types of data. Examples of the data stored in the storage unit 52 include image data of the OCT image, image data of the fundus image, scan data, image data of the anterior eye segment image, and information of the eye to be examined. The information of the eye to be examined includes information regarding the subject such as a patient ID and a name, information regarding the eye to be examined such as identification information of the left eye or right eye, and the like.

Furthermore, an eyeball parameter 52A is stored in the storage unit 52. The eyeball parameter 52A includes a parameter (standard value) defined in a known eyeball model such as the Gullstrand model eye. In some embodiments, the eyeball parameter 52A includes parameters in which at least one of the parameters defined in the known eyeball model is replaced with the measurement value of the eye to be examined E. In this case, it means that the eyeball parameter 52A includes a parameter representing an optical property of the eye to be examined E. The measurement value includes an axial length, a corneal thickness, a radius of curvature of the anterior corneal surface, a radius of curvature of the posterior corneal surface, an anterior chamber depth, a radius of curvature of the anterior lens surface, a lens thickness, a radius of curvature of the posterior lens surface, a vitreous cavity length, a retinal thickness, a choroid thickness, or the like. In some embodiments, the measurement value is acquired by analyzing OCT data obtained by the OCT measurement. The eyeball parameter 52A may include a parameter specified by the UI unit 8 to be described below.

Furthermore, various programs and data for operating the ophthalmic device 1 are stored in the storage unit 52.

Image Forming Unit

The image forming unit 6 forms a tomographic image (OCT image) of the eye to be examined E from the scan data having been obtained by scanning the interior of the eye with the measurement light using an optical scanner disposed optically substantially conjugate with respect to a predetermined site (for example, the pupil) of the eye to be examined E. The image forming unit 6 forms a reflection intensity profile of an A-line by performing signal processing such as Fourier transform on the sampling data having been obtained by sampling, using the DAQ, a detection signal from the detector in the interference optical system 40. The above signal processing includes noise removal (noise reduction), filtering, Fast Fourier Transform (FFT), and the like. The reflection intensity profile of the A-line is an example of A-scan data. The image forming unit 6 is able to form B-scan data (two-dimensional scan data) by forming reflection intensity profiles for each A-line and arranging the plurality of formed reflection intensity profiles in a B-scan direction (a direction intersecting with the A-scan direction).

In some embodiments, the image forming unit 6 (or the data processing unit 7 to be described below) arranges the plurality of reflection intensity profiles formed for each A-line in the B-scan direction (for example, x-direction) and a direction intersecting with the A-scan direction and the B-scan direction (for example, y-direction), thereby forming three-dimensional scan data.

Further, the image forming unit 6 is able to form an A-scan image (OCT image, image data) of the eye to be examined E by imaging the reflection intensity profile of the A-line. The image forming unit 6 is able to form a B-scan image by arranging a plurality of A-scan images formed for each A-line in the B-scan direction (the direction intersecting with the A-scan direction).

In some embodiments, the image forming unit 6 extracts data at a predetermined depth position (scan position) in each A-scan data, and arranges the plurality of extracted data in the B-scan direction (the direction intersecting with the A-scan direction) to form C-scan data. In some embodiments, the image forming unit 6 extracts pixels at a predetermined depth position (scan position) in each A-scan image, and arranges the plurality of extracted pixels in the B-scan direction (the direction intersecting with the A-scan direction) to form a C-scan image.

In some embodiments, the functions of the image forming unit 6 are enabled by a processor. Note that in this specification, "image data" and an "image" based on the image data may be considered to be the same.

Data Processing Unit 7

The data processing unit 7 performs various types of data processing. An example of data processing is processing of image data formed by the image forming unit 6 or other devices. Examples of this processing include image processing, image analysis, image evaluation, and diagnostic assistance. The data processing unit 7 performs correction processing such as luminance correction and dispersion correction of the image. In addition, the data processing unit 7 performs various image processing and analysis processing on the fundus image, tomographic image, and the like. The data processing unit 7 performs known image processing such as interpolation processing that interpolates pixels between the tomographic images, thereby making it possible to form volume data (voxel data) of the eye to be examined E. When an image based on the volume data is to be displayed, the data processing unit 7 performs rendering processing on the volume data to form a pseudo three-dimensional image when viewed from a specific line of sight.

The data processing unit 7 is able to form a C-mode image, a projection image, and a shadowgram from the volume data. The C-mode image is formed by selecting pixels (pixels, voxels) on a specified cross section from a three dimensional data set. The projection image is formed by projecting the three-dimensional data set in a predetermined direction (Z direction, depth direction, axial direction). The shadowgram is formed by projecting part of the three-dimensional data set (for example, partial data corresponding to an identified layer) in a predetermined direction.

Further, the data processing unit 7 is able to generate an image of the entire scan area AR by positioning images adjacent to each other with respect to the plurality of images (tomographic images) obtained from the plurality of sub-scan areas. At this time, the data processing unit 7 may make use of the overlapping areas to position the adjacent images.

The data processing unit 7 is able to construct a B-mode image in which a retinal vessel, choroid vessel and the like are highlighted, a front image (vascular highlighting image, angiogram), and the like based on the data collected in time series by OCT (for example, B-scan image data). For example, OCT data in time series may be collected by repeatedly scanning approximately the same site of the eye to be examined E.

In some embodiments, the data processing unit 7 compares the B-scan images in time series obtained by the B-scan with respect to approximately the same site, and converts a pixel value of a signal intensity changing portion to a pixel value corresponding to the amount of change in signal intensity, thereby constructing a highlighting image in which the above changing portion is highlighted. Furthermore, the data processing unit 7 extracts information of an amount corresponding to a predetermined thickness at a desired site from a plurality of constructed highlighting images to construct an en-face image, thereby forming an OCTA image.

In addition, the data processing unit 7 analyzes a detection result of interference light obtained by the OCT measurement, and determines a focus state of the measurement light in the focus fine adjustment control. For example, the main control unit 51 performs the OCT measurement repeatedly while controlling the focusing lens of the interference optical system 40 in accordance with a predetermined algorithm. The data processing unit 7 calculates a predetermined evaluation value regarding image quality of the OCT image by analyzing the detection result of the interference light acquired iteratively by the OCT measurement. The data processing unit 7 determines whether the calculated evaluation value is less than or equal to a threshold value. In some embodiments, the focus fine adjustment is continuously carried out until the calculated evaluation value becomes equal to or less than the threshold value. That is, the focus state of the measurement light is judged to be appropriate when the evaluation value is equal to or less than the threshold value, and the focus fine adjustment is carried out until the focus state of the measurement light is judged to be appropriate.

In some embodiments, the main control unit 51 monitors the intensity (interference intensity, interference sensitivity) of the interference signals acquired sequentially while repeatedly performing the OCT measurement as described above to acquire the interference signals. Furthermore, while the above-discussed monitoring processing being performed, the position of the focusing lens is searched in such a manner that the interference intensity becomes maximum by moving the focusing lens of the interference optical system 40. According to such focus fine adjustment, it is possible to guide the focusing lens to a position where the interference intensity is optimized.

The data processing unit 7 analyzes the detection result of the interference light obtained by the OCT measurement, and determines a polarization state of at least one of the measurement light and the reference light. For example, the main control unit 51 repeatedly performs the OCT measurement while controlling the polarization controller in accordance with a predetermined algorithm. In some embodiments, the main control unit 51 controls the optical attenuator to change the attenuation of the reference light. The data processing unit 7 calculates a predetermined evaluation value regarding image quality of the OCT image by analyzing the detection result of the interference light acquired iteratively by the OCT measurement. The data processing unit 7 determines whether the calculated evaluation value is less than or equal to a threshold value. The threshold value is set in advance. The polarization adjustment is continuously carried out until the calculated evaluation value becomes less than or equal to the threshold value. That is, the polarization state of the measurement light is judged to be appropriate when the evaluation value is equal to or less than the threshold value, and the polarization adjustment is carried out until the polarization state of the measurement light is judged to be appropriate.

In some embodiments, the main control unit 51 is able to monitor the interference intensity also in the polarization adjustment.

Moreover, the data processing unit 7 performs predetermined analysis processing on a detection result of the interference light obtained by the OCT measurement or on an OCT image formed based on the detection result. The predetermined analysis processing includes identifying predetermined sites (tissues, lesions) in the eye to be examined E; calculating a distance (interlayer distance) between specified sites, an area, an angle, a ratio, and density; arithmetic operation using a specified formula; identifying the shape of a predetermined site; calculating statistics thereof; calculating distribution of the measurement values and the statistics; image processing based on these analysis processing results; and the like. The predetermined tissues include a blood vessel, optic papilla, fovea, macula, and the like. The predetermined lesions include a white spot, bleeding, and the like.

The data processing unit 7 rotates a tomographic image acquired by using the OCT while making the measurement optical axis be eccentric relative to a predetermined side (for example, the fovea or macular region) of the eye to be examined E, about a predetermined reference position in accordance with an eccentric amount and an eccentric direction of the measurement optical axis relative to the predetermined site. As a result, it is easy to grasp an OCT measurement position based on the predetermined site.

In some embodiments, the data processing unit 7 performs coordinate transformation of the pixel positions in the OCT image or the scan positions in the scan data, such that the site at the interior of the eye in the acquired OCT image (tomographic image, scan data) is depicted in the actual shape.

A comparative example of the embodiment will now be described.

Figure 4:
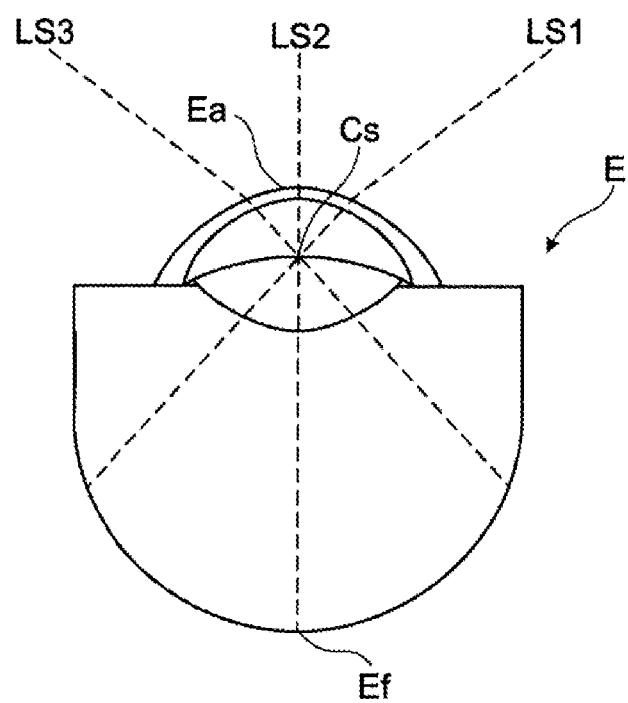
FIG. 4 is a schematic diagram for describing a process performed by an ophthalmic device according to a comparative example of an embodiment.
Figure 5:
FIG. 5 is a schematic diagram for describing a process performed by an ophthalmic device according to a comparative example of an embodiment.

FIGS. 4 and 5 illustrate descriptive diagrams of the comparative example of the embodiment. FIG. 4 schematically illustrates a path of measurement light incident on the eye to be examined E. FIG. 5 depicts an example of a tomographic image obtained by scanning with the measurement light incident on the eye to be examined E through the path illustrated in FIG. 4.

For example, measurement light deflected by the optical scanner of the scanning optical system 30 is incident on the pupil of the eye to be examined E as the scanning center position, at various angles of incidence as illustrated in FIG. 4. The measurement light incident on the eye to be examined E is projected toward the sites inside the eye while being centered on a scanning center position Cs set in the pupil center, for example.

An A-scan image is formed from interference data obtained by using measurement light LS1 in FIG. 4, an A-scan image is formed from interference data obtained by using measurement light LS2, and an A-scan image is formed from interference data obtained by using measurement light LS3. A tomographic image IMG0 of the fundus illustrated in FIG. 5 is formed by arranging a plurality of A-scan images having been formed in this manner.

As described above, the A-scan direction changes within a scanning angle range centered at the scanning center position Cs, and the shape of the site is deformed in the tomographic image in which the plurality of A-scan images obtained are arranged in a lateral direction. Due to this, a difference in shape from the actual shape increases as the angle of view increases.

Form information representing the form of the eye to be examined E is determined by the position of any pixel in the tomographic image. Such form information includes an intraocular distance (including a distance between layer regions), an area of a region, a volume of the region, a circumference length of the region, a direction of a site relative to the reference position, an angle of the site relative to the reference direction, a radius of curvature of the site, and the like.

For example, the intraocular distance as the form information may be determined by measuring a distance between any two points in the tomographic image. In this case, the distance between the two points is identified by the number of pixels in the tomographic image, and is measured by multiplying the identified number of pixels by a device-specific pixel size. At this time, the same pixel size is employed for all pixels in the tomographic image. However, as described above, since the scanning directions are different centered on the scanning center position Cs, pixel sizes in the horizontal direction of the tomographic image differ depending on a depth position in the scanning direction. For example, in a case where a depth range is 2.5 [mm], when the same pixel size is employed for all pixels in the tomographic image, there is a difference of about 13% in a scan length of the B-scan between the upper and lower portions of the tomographic image; in a case where the depth range is 10 [mm], a difference of about 50% is generated.

Thus, the data processing unit 7 according to the embodiment performs coordinate transformation of the pixel positions in the acquired OCT image or the scan positions in the scan data. The data processing unit 7 performs the above-described rotation processing on the tomographic image (scan data) having experienced the coordinate transformation. In some embodiments, the data processing unit 7 performs coordinate transformation on the OCT image rotated as described above. Hereinafter, as the form information representing the form of the eye to be examined E, the intraocular distance is exemplified and explained.

Figure 6:
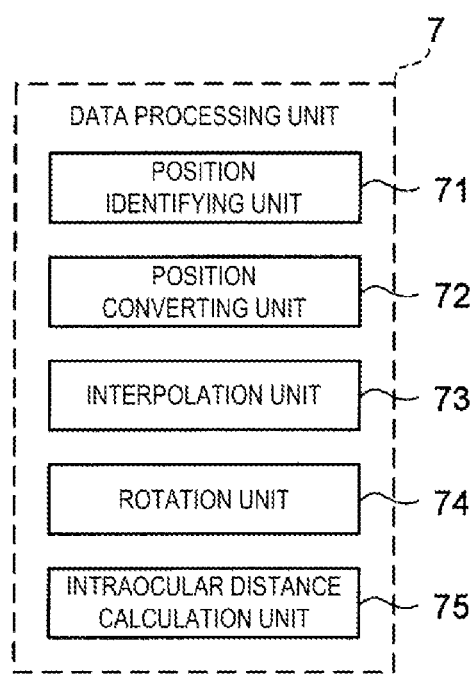
FIG. 6 is a schematic block diagram illustrating an example of a configuration of an ophthalmic device according to an embodiment.

FIG. 6 illustrates a block diagram of a configuration example of the data processing unit 7 according to the embodiment.

The data processing unit 7 includes a position identifying unit 71, a position converting unit 72, an interpolation unit 73, a rotation unit 74, and an intraocular distance calculation unit 75.

Position Identifying Unit

Figure 7:
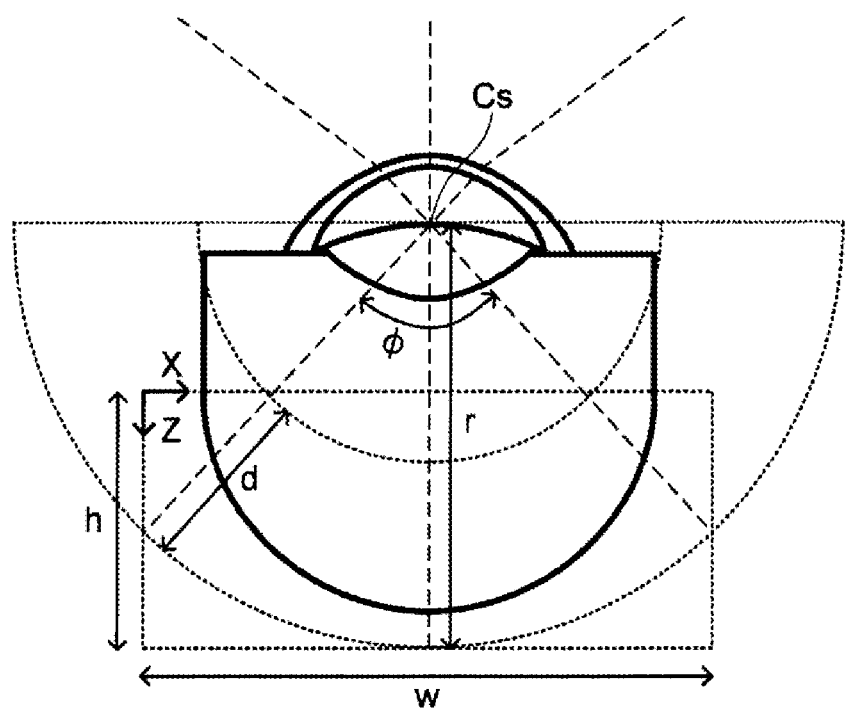
FIG. 7 is a schematic diagram for describing a process performed by an ophthalmic device according to an embodiment.

The position identifying unit 71 identifies a conversion position, which corresponds to a pixel position in the acquired OCT image (or scan position in the scan data), along a traveling direction of the measurement light passing through the scanning center position Cs (see FIG. 7). In some embodiments, the position identifying unit 71 uses the eyeball parameter 52A in the identifying processing of the conversion position.

FIG. 7 illustrates a descriptive diagram of operation of the position identifying unit 71 according to the embodiment. In FIG. 7, constituent elements similar to those in FIG. 4 are denoted by the same reference signs, and description thereof will be omitted as appropriate.

Assume that a scanning angle is defined as $\varphi$, a scanning radius is defined as r, a depth range in which the OCT measurement is possible to be carried out is defined as d, a length in the depth direction of a tomographic image is defined as h, and a length in the lateral direction of the tomographic image is defined as w. The scanning angle $\varphi$ corresponds to the deflection angle of the measurement light centered on the scanning center position Cs. The scanning radius r corresponds to a distance from the scanning center position Cs to a position of a light path length being zero where the measurement light path length is substantially equal to the reference light path length. The depth range d is a device-specific value (known value) that is uniquely determined by optical design or the like of the device.

The position identifying unit 71 identifies a conversion position (X, Z) in a second coordinate system from a pixel position (x, z) in a first coordinate system. The first coordinate system takes a coordinate position in the upper left of the OCT image (B-scan image) as the origin, and is defined by an x-coordinate axis taking the B-scan direction as an x-direction and a z-coordinate axis that is orthogonal to the x-coordinate axis and takes the A-scan direction as a z-direction. The pixel position (x, z) in the OCT image is defined in the first coordinate system. The second coordinate system is defined by a Z coordinate axis (for example, a second axis) taking, as a Z direction, a traveling direction of the measurement light with a scanning angle being 0 degrees relative to the measurement optical axis passing through a predetermined site (for example, the fovea) at the fundus Ef, and an X coordinate axis (for example, a first axis) taking, as an X direction, the B-scan direction orthogonal to the Z coordinate axis at the predetermined site. In the second coordinate system, a predetermined Z position is taken as the origin of the Z coordinate axis in such a manner that the position of the scanning radius r is the deepest portion of the measurement optical axis passing through a predetermined site (for example, the fovea). In addition, as described below, a predetermined X position of the measurement optical axis passing through a predetermined site (for example, the fovea) is taken as the origin of the X coordinate axis in such a manner as to obtain a length d in a predetermined depth direction. The conversion position (X, Z) is defined in the second coordinate system. The conversion position (X, Z) corresponds to the pixel position (x, z), and is a position along the traveling direction (A-scan direction) of the measurement light passing through the scanning center position Cs.

The position identifying unit 71 identifies the conversion position (X, Z) with respect to the OCT image based on the scanning radius r in the A-scan direction, the scanning angle φ, the depth range d in which the OCT measurement is possible to be carried out, and the pixel position (x, z). The position identifying unit 71 is able to identify at least one of an X component (component in the first axis direction) and a Z component (component in the second axis direction) of the conversion position.

For the OCT image (tomographic image) where the number of A-scan lines is N (N is a natural number), the conversion position (X, Z) corresponding to the pixel position (x, z) in the n-th A-scan line (n is a natural number) is identified as indicated by Equation (1) and Equation (2).

[Equation 1]
$$X = \frac{w}{2} + (r - d + z) \times \sin\left(\frac{\phi}{N} \times n - \frac{\phi}{2}\right) \quad (1)$$

[Equation 2]
$$Z = (r - d + z) \times \cos\left(\frac{\phi}{N} \times n - \frac{\phi}{2}\right) - (r - d) \times \cos\frac{\phi}{2} \quad (2)$$

Here, the length h in the depth direction, the length w in the lateral direction, and the x component of the pixel position of the OCT image are expressed as in Equation (3) to Equation (5).

[Equation 3]
$$h = r - (r - d) \times \cos\frac{\phi}{2} \quad (3)$$

[Equation 4]
$$w = 2r \times \sin\frac{\phi}{2} \quad (4)$$

[Equation 5]
$$x = n \quad (5)$$

In Equations (1) and (2), the x-coordinate of the pixel position is expressed as in Equation (5). Accordingly, the position identifying unit 71 is able to identify the conversion position (X, Z) from the pixel position (x, z) based on the scanning radius r, the scanning angle φ, and the depth range d.

In some embodiments, for the scan data, the position identifying unit 71 is able to identify the conversion position (X, Z), in the same manner as described above, based on the scanning radius r in the A-scan direction, the scanning angle φ, the depth range d in which the OCT measurement is possible to be carried out, and the scan position.

In some embodiments, the scanning radius r is identified by analyzing the detection result of the interference light obtained by the interference optical system 40. This makes it possible to identify the conversion position (X, Z) reflecting more accurately the optical properties of the eyeball of the eye to be examined E.

In some embodiments, the position identifying unit 71 identifies the scanning angle φ by performing ray tracking processing on the measurement light based on the corneal shape information of the eye to be examined E. The corneal shape information may include a corneal curvature radius (radius of curvature of an anterior corneal surface, radius of curvature of a posterior corneal surface), a corneal thickness, and the like. This makes it possible to identify the conversion position (X, Z) reflecting more accurately the optical properties of the eyeball of the eye to be examined E.

Position Converting Unit

The position converting unit 72 converts the pixel position (x, z) of the OCT image to the conversion position (X, Z) identified by the position identifying unit 71. In some embodiments, for each of all the pixel positions in the OCT image, the position identifying unit 71 identifies the conversion position, and the position converting unit 72 converts the pixel position to the conversion position.

Figure 8:
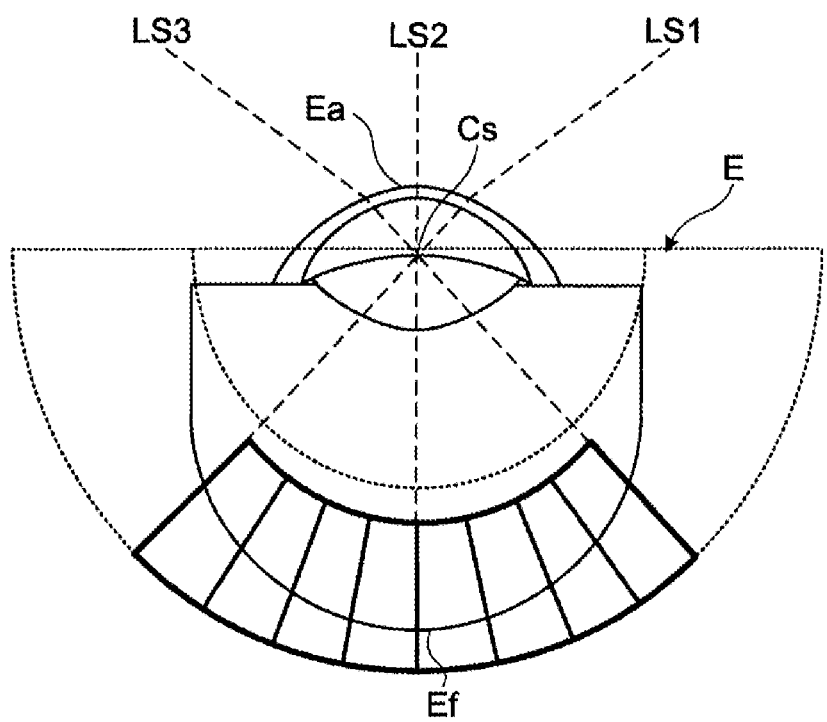
FIG. 8 is a schematic diagram for describing a process performed by an ophthalmic device according to an embodiment.

As a result, as illustrated in FIG. 8, it is possible for the A-scan images acquired by A-scan to be arranged in the A-scan direction. Therefore, even in the case where the angle of view is wide, a tomographic image in which the shape of a predetermined site is the same as the actual shape may be acquired, as in a tomographic image IMG1 illustrated in FIG. 9.

Figure 9:
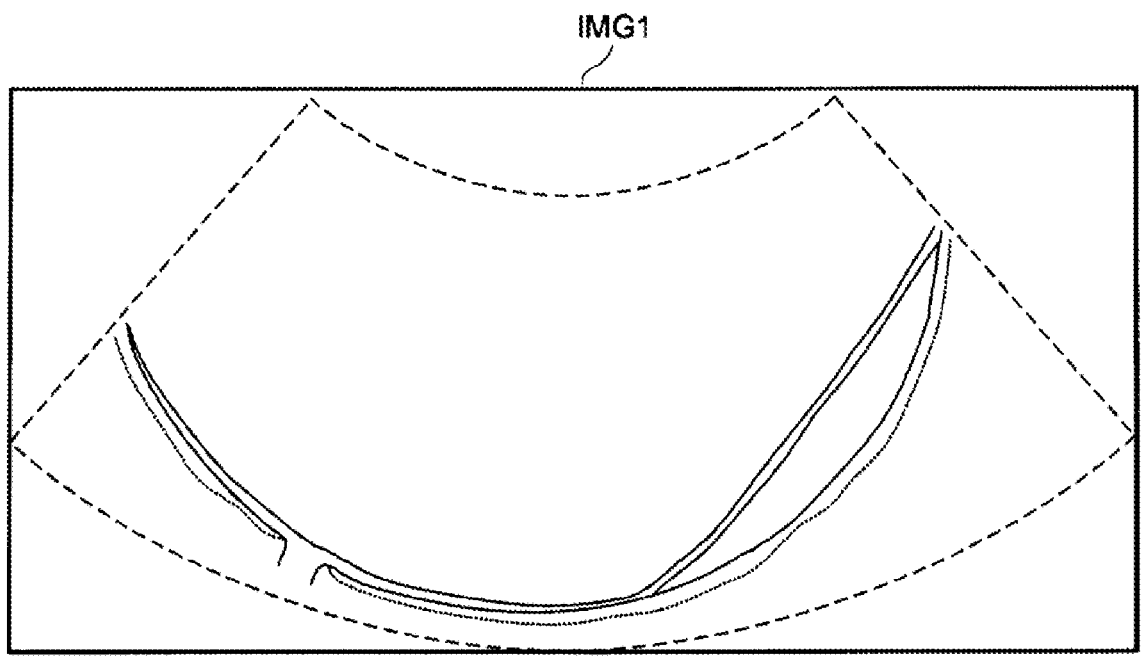
FIG. 9 is a schematic diagram for describing a process performed by an ophthalmic device according to an embodiment.

For example, both the tomographic image IMG0 illustrated in FIG. 5 and the tomographic image IMG1 illustrated in FIG. 9 are tomographic images of the fundus Ef in which retinal separation has occurred. In the tomographic image IMG1, since the separation state of the neural retina over a wide range of the fundus Ef is depicted as the actual form, it is easier to grasp the above-mentioned separation state than in the tomographic image IMG0.

Interpolation Unit

The interpolation unit 73 interpolates pixels between the conversion positions. For example, as described above, in accordance with the distance from the scanning center position Cs, the pixel positions are converted to the conversion positions so that intervals between adjacent A-scan images are changed. The interpolation unit 73 interpolates pixels between the A-scan images by using the pixels of the A-scan images adjacent to each other in accordance with the depth positions of the A-scan images. As interpolation processing of pixels by the interpolation unit 73, it is possible to employ a known method such as a nearest-neighbor method, a bilinear interpolation method, a bicubic interpolation method, or the like. In some embodiments, the interpolation unit 73 interpolates pixels between the A-scan images adjacent to each other in accordance with the distance from the scanning center position Cs. For example, the interpolation unit 73 changes the interpolation processing method in accordance with the distance from the scanning center position Cs, and then interpolates pixels between the A-scan images adjacent to each other.

In some embodiments, the scan data is interpolated with respect to the scan positions of the scan data, similarly to the above.

Rotation Unit

The rotation unit 74 rotates the tomographic image after the converting processing by the position converting unit 72 or the tomographic image after the interpolation processing by the interpolation unit 73. The rotation unit 74 rotates the tomographic image in accordance with the eccentric amount and the eccentric direction of the measurement optical axis O relative to a predetermined site of the fundus Ef. The predetermined site of the fundus Ef includes a fovea, macular region, lesion site, blood vessel, and the like. The eccentric amount corresponds to, for example, a distance in the xy direction between a predetermined site at the fundus Ef and the measurement optical axis O. The eccentric direction corresponds to, for example, the direction of the measurement optical axis O relative to the predetermined site at the fundus Ef.

Figure 10:
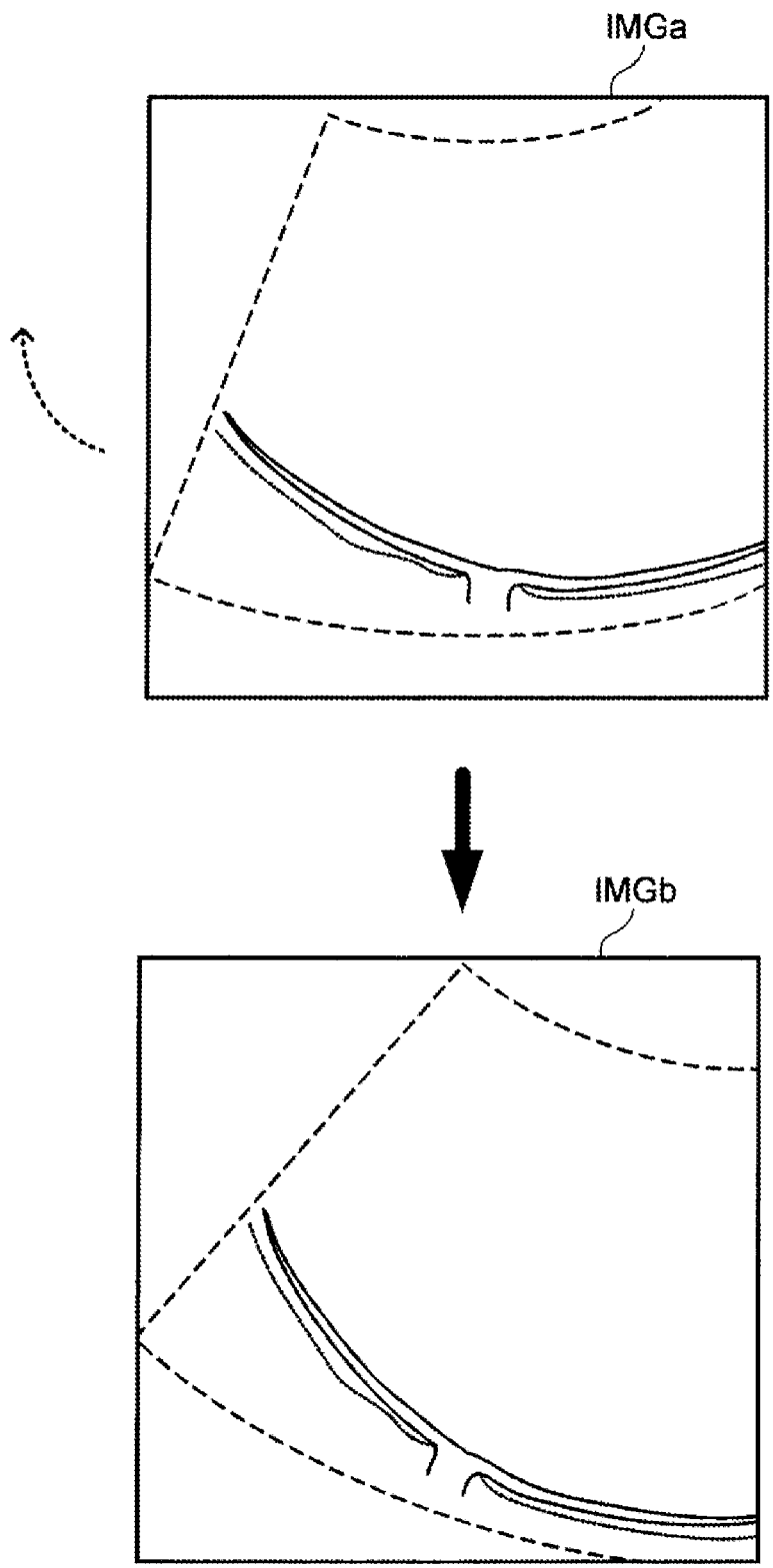
FIG. 10 is a schematic diagram for describing a process performed by an ophthalmic device according to an embodiment.

FIG. 10 illustrates a descriptive diagram of operation of the rotation unit 74 according to the embodiment.

The rotation unit 74 acquires the eccentric amount and the eccentric direction, and identifies the rotation angle and rotation direction of a tomographic image IMGa from the acquired eccentric amount and eccentric direction. The rotation unit 74 rotates the tomographic image IMGa at the identified rotation angle and in the identified rotation direction about a predetermined reference position in the tomographic image IMGa after being processed by the position converting unit 72 or the interpolation unit 73, for example, and outputs a tomographic image IMGb after being rotated. The predetermined reference position is a pixel position on the tomographic image corresponding to the scanning center position Cs on the measurement optical axis O, or the like.

In some embodiments, the optical system 2 is revolved relative to the pupil position of the eye to be examined E by at least one of the swing mechanism 4B and the tilt mechanism 4C, so that the OCT measurement is performed while making the measurement optical axis O be eccentric relative to the fovea of the eye to be examined E at the fundus Ef. In this case, the eccentric amount is determined by using at least one of a swing amount and a tilt amount of the optical system 2 based on the pupil position of the eye to be examined E. The eccentric direction is determined by using at least one of a swing direction and a tilt direction of the optical system 2 based on the pupil position of the eye to be examined E. For example, the main control unit 51 or the rotation unit 74 identifies the eccentric amount and the eccentric direction based on the contents of control with respect to at least one of the swing mechanism 4B and the tilt mechanism 4C (or the drive unit 4D). In some embodiments, it is possible for the main control unit 51 or the rotation unit 74 to identify the eccentric amount and the eccentric direction based on a detection result obtained by an encoder, a position sensor, or the like configured to detect at least one of a swing state of the optical system 2 by the swing mechanism 4B and a tilt state of the optical system 2 by the tilt mechanism 4C.

In some embodiments, the projection position of the fixation light flux at the fundus Ef is made eccentric from the measurement optical axis O, so that the OCT measurement is performed by making the measurement optical axis O be eccentric relative to the fovea of the eye to be examined E at the fundus Ef. In this case, the eccentric amount is determined by using the amount of displacement of the projection position of the fixation light flux relative to the measurement optical axis O at the fundus Ef. The eccentric direction is determined by using a displacement direction of the projection position of the fixation light flux relative to the measurement optical axis O at the fundus Ef. For example, the main control unit 51 or the rotation unit 74 identifies the eccentric amount and the eccentric direction based on the contents of control with respect to the fixation optical system 50. In some embodiments, the main control unit 51 or the rotation unit 74 identifies the eccentric amount and the eccentric direction by analyzing the fundus image acquired by the observation optical system 20 or the like.

Intraocular Distance Calculation Unit

The intraocular distance calculation unit 75 calculates the intraocular distance of the eye to be examined E based on at least the OCT image converted by the position converting unit 72.

The intraocular distance calculation unit 75 determines the intraocular distance between predetermined sites of the eye to be examined E based on the OCT image converted by the position converting unit 72. For example, the intraocular distance calculation unit 75 identifies the predetermined sites inside the eye by analyzing the converted OCT image, and then determines the intraocular distance based on the distance between the identified sites. The distance between two points is identified by the number of pixels in the tomographic image, and is measured by multiplying the identified number of pixels by a device-specific pixel size. At this time, the same pixel size is employed for all pixels in the tomographic image.

As the intraocular distance between the predetermined sites, the following may be cited: a distance between specified sites (tissues, layer regions), an axial length, a distance from the scanning center position of the measurement light set to the pupil center or the like, and the like. When the axial length is to be determined as the intraocular distance, the intraocular distance calculation unit 75 determines the axial length based on the distance from a site corresponding to the corneal apex to a site corresponding to the retina.

In some embodiments, the intraocular distance calculation unit 75 calculates the intraocular distance of the eye to be examined E in the same manner as described above, based on the scan data in which the scan position is converted to the conversion position by the position converting unit 72.

The data processing unit 7 according to some embodiments further includes a size adjustment unit configured to adjust the size of a tomographic image. The size adjustment unit adjusts the sizes in the horizontal and vertical directions of the tomographic image rotated by the rotation unit 74. The size adjustment unit is able to adjust the sizes in the horizontal and vertical directions of the tomographic image in such a manner that the size of a predetermined site in the tomographic image takes a predefined reference size. For example, the size adjustment unit adjusts the sizes in the horizontal direction and vertical direction of the tomographic image in such a manner that the radius of curvature of a predetermined layer region (for example, a retinal pigment epithelium layer) obtained by analyzing the tomographic image having been converted by at least the position converting unit 72 takes a predefined size.

The data processing unit 7 according to some embodiments further includes a site identifying unit configured to identify a characteristic site. The site identifying unit analyzes a tomographic image to identify a predetermined site (for example, a macular region). The rotation unit 74 is able to perform image rotation processing on the tomographic image in such a manner that the predetermined site identified by the site identifying unit is arranged at a predefined position (for example, the lowermost portion of the image). Further, the rotation unit 74 is able to perform image rotation processing on the tomographic image having been rotated in accordance with the eccentric amount and the eccentric direction in such a manner that the predetermined site identified by the site identifying unit is arranged at a predefined position. With this, for example, a tomographic image with a macular region arranged at the lowermost portion may be acquired, thereby making it easy to identify the desired site in the tomographic image representing the actual shape.

The data processing unit 7 that functions as described above includes, for example, the afore-mentioned processor, a RAM, a ROM, a hard disk drive, a circuit board, and the like. A storage device such as a hard disk drive stores, in advance, a computer program that causes the processor to execute the above-described functions.

User Interface Unit

The user interface (UI) unit 8 has a function of exchanging information between a user and the ophthalmic device 1. The user interface unit 8 includes a display device and an operation device (input device). The display device includes, for example, a liquid crystal display (LCD). The operation device includes various hardware keys and/or software keys. The controller 5 receives the content of operation with respect to the operation device, and outputs a control signal corresponding to the content of operation to each constituent element. At least part of the operation device and at least part of the display device may be integrally constituted. A touch panel display is one example thereof.

As described above, the display control unit 51A controls the display device of the UI unit 8 to display various images. In particular, the display control unit 51A is able to cause the display device to display a tomographic image formed by the image forming unit 6 and a tomographic image after being processed by the data processing unit 7. The display control unit 51A is able to simultaneously display a tomographic image formed by the image forming unit 6 and a tomographic image after being processed by the data processing unit 7 on the same screen of the display device. As the tomographic image after being processed by the data processing unit, there are cited a tomographic image converted by the position converting unit 72, a tomographic image interpolated by the interpolation unit 73, a tomographic image rotated by the rotation unit 74, and the like.

Figure 11:
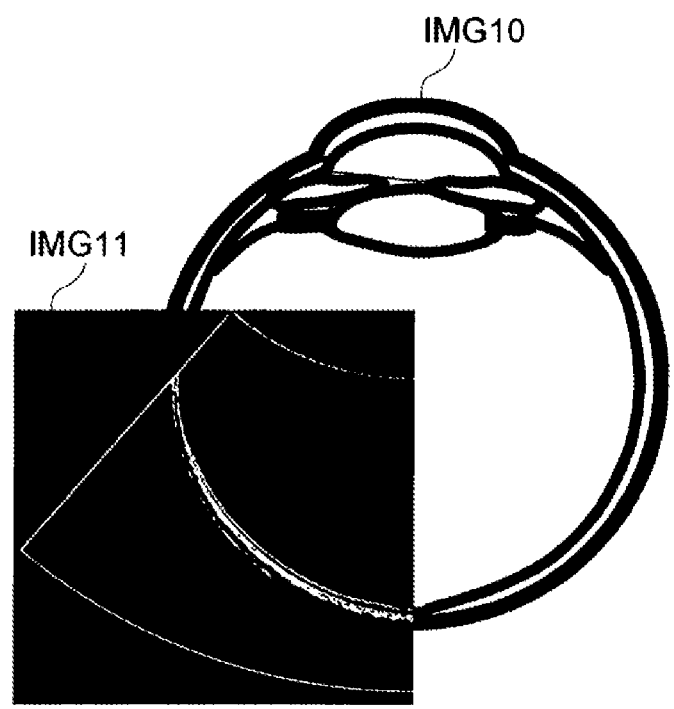
FIG. 11 is a schematic diagram for describing a process performed by an ophthalmic device according to an embodiment.

In some embodiments, the display control unit 51A causes the display device to display a tomographic image IMG11 rotated by the rotation unit 74 in such a manner that the tomographic image IMG11 is superimposed on an image (model image) IMG10 representing a cross-sectional structure of the eye, as illustrated in FIG. 11. As the image IMG10 representing the cross-sectional structure of the eye, there are cited computer graphics, drawings, illustrations, separately acquired images (still images, videos), photographs, and the like. The images and photographs may be of the same eye to be examined or of another eye to be examined. For example, the data processing unit 7 identifies a characteristic site in the tomographic image IMG11 (or the tomographic image before rotation). The display control unit 51A causes the tomographic image IMG11 to be superimposed on the image IMG10 and displayed in such a manner that the identified characteristic site is arranged at a position corresponding to the characteristic site in the image IMG10.

In some embodiments, the display control unit 51A adjusts the size of the image IMG10 based on (the size of) the tomographic image IMG11, and causes the display device to display the tomographic image IMG11 rotated by the rotation unit 74 in such a manner that the tomographic image IMG11 is superimposed on the image IMG10 having the adjusted size. In some embodiments, the data processing unit 7 (or the display control unit 51A) adjusts the size of the image IMG10 based on the intraocular distance (or the form information) determined by the intraocular distance calculation unit 75. For example, the data processing unit 7 adjusts the size of the image IMG10 to match the radius of curvature of the fundus Ef (a predetermined layer region such as a retinal pigment epithelium layer) determined by the intraocular distance calculation unit 75. In some embodiments, the display control unit 51A adjusts the size of the tomographic image IMG11 based on (the size of) the image IMG10, and causes the display device to display the tomographic image IMG11 rotated by the rotation unit 74 in such a manner that the tomographic image IMG11 is superimposed on the image IMG10.

Figure 12:
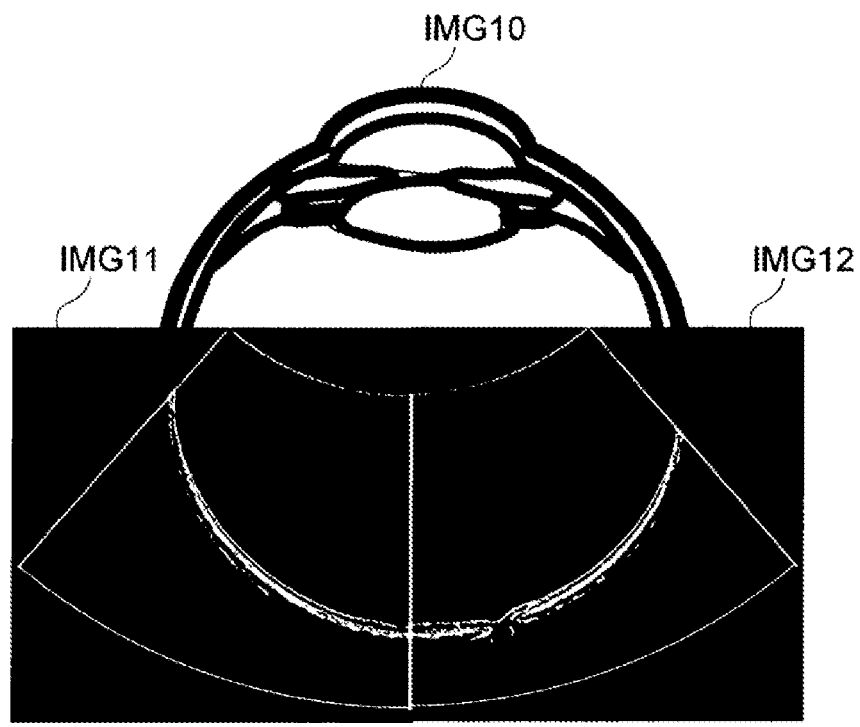
FIG. 12 is a schematic diagram for describing a process performed by an ophthalmic device according to an embodiment.

In some embodiments, the display control unit 51A causes the display device to display two or more tomographic images IMG11 and IMG12 rotated by the rotation unit 74 in such a manner that the two or more tomographic images are superimposed on the image IMG10 representing a cross-sectional structure of the eye, as illustrated in FIG. 12. Note that the tomographic image IMG12 is a tomographic image acquired in an eccentric amount and an eccentric direction different from those of the tomographic image IMG11. In FIGS. 11 and 12, a case is described in which a tomographic image of the fundus Ef is displayed, but an anterior eye segment image of the eye to be examined E may be displayed instead.

The rotation unit 74 is an example of the "image rotation unit" according to the embodiment. The position converting unit 72 is an example of the "converting unit" according to the embodiment. The display device of the UI unit 8 is an example of the "display device" according to the embodiment. The interference optical system 40, the scanning optical system 30, and the image forming unit 6 (or the data processing unit 7) are an example of the "OCT unit" according to the embodiment.

Operation

Operation of the ophthalmic device 1 according to the embodiment will be described.

Figure 13:
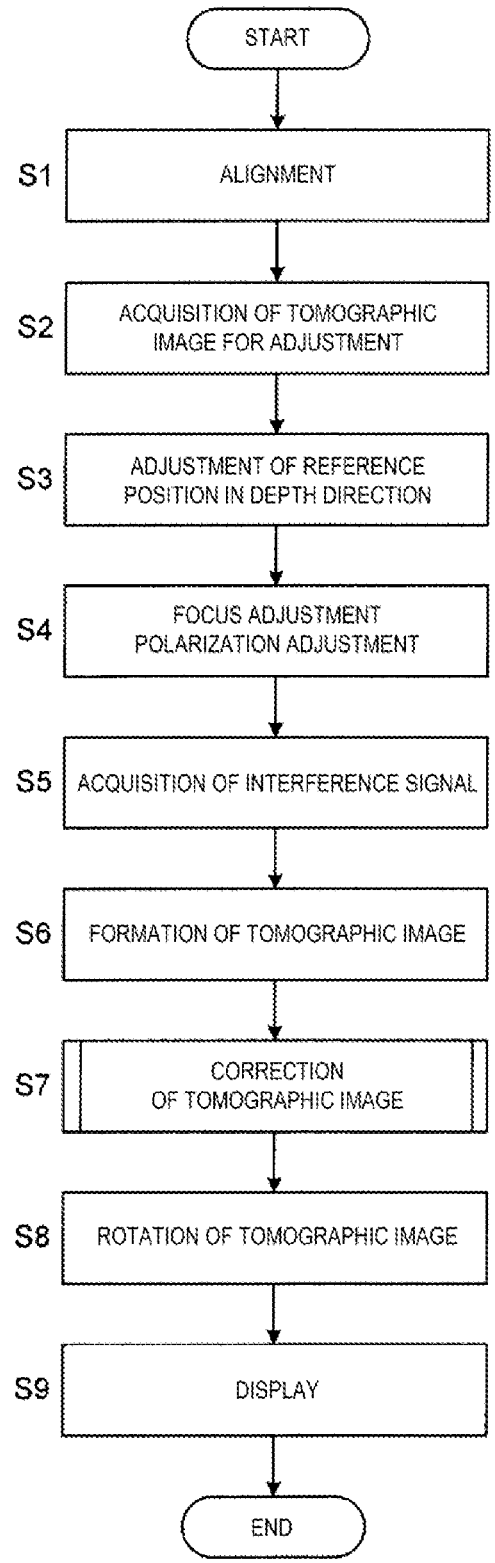
FIG. 13 is a flowchart illustrating an operation example of an ophthalmic device according to an embodiment.
Figure 14:
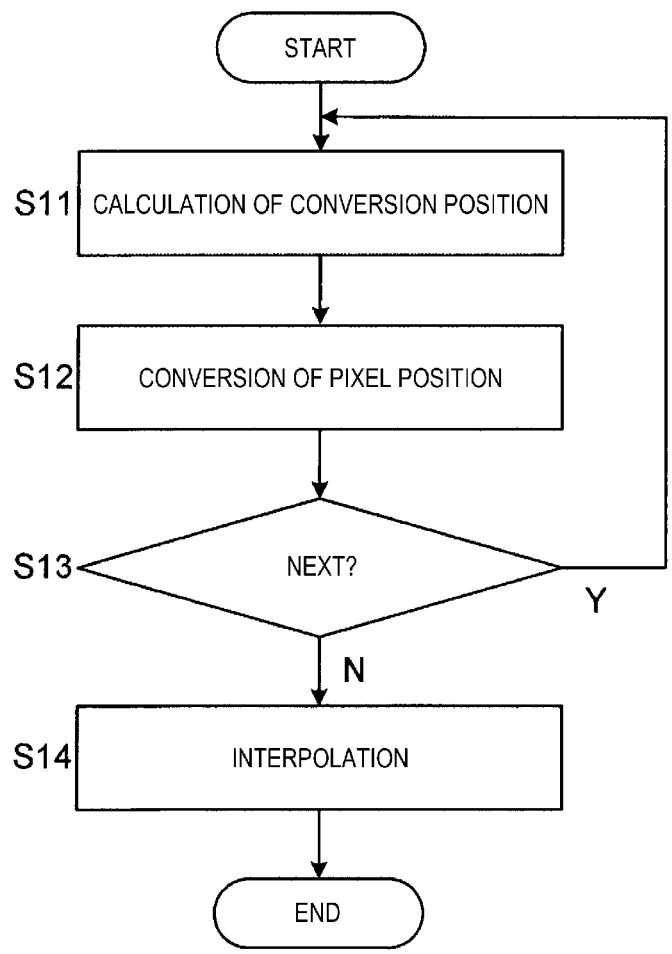
FIG. 14 is a flowchart illustrating an operation example of an ophthalmic device according to an embodiment.

FIGS. 13 and 14 illustrate an operation example of the ophthalmic device 1 according to the embodiment. FIGS. 13 and 14 depict flowcharts of the operation example of the ophthalmic device 1 according to the embodiment. FIG. 14 depicts a flowchart of an operation example of step S7 in FIG. 13. A computer program for achieving processing illustrated in FIGS. 13 and 14 is stored in the storage unit 52. The main control unit 51 performs the processing illustrated in FIGS. 13 and 14 by operating in accordance with the computer program.

S1: Alignment

The main control unit 51 performs alignment.

For example, the main control unit 51 controls an alignment system (not illustrated) to project an alignment indicator onto the eye to be examined E. At this time, fixation light flux is projected onto the eye to be examined E at a predetermined projection position (for example, a projection position on the measurement optical axis O) by the fixation optical system 50. The main control unit 51 controls the xyz movement mechanism 4A based on the amount of movement of the optical system 2 that is identified based on a light-receiving image acquired by the observation optical system 20, and moves the optical system 2 relative to the eye to be examined E by the amount of movement. The main control unit 51 makes this processing performed repeatedly.

In some embodiments, after the alignment in step S1 is completed, the alignment roughness adjustment and alignment fine adjustment are carried out.

S2: Acquisition of Tomographic Image for Adjustment

The main control unit 51 causes fixation light flux for the OCT measurement to be projected to a position on the measurement optical axis O at the fundus Ef, for example.

Next, the main control unit 51 controls the scanning optical system 30 and the interference optical system 40 to perform OCT temporary measurement so as to acquire a tomographic image for adjustment to be used for adjusting a reference position of the measurement range in the depth direction. Specifically, the main control unit 51 controls the optical scanner of the scanning optical system 30 to deflect the measurement light generated based on the light emitted from the OCT light source, and causes a predetermined site of the eye to be examined E (for example, the fundus Ef) to be scanned with the deflected measurement light. The detection result of interference light obtained by scanning with the measurement light is sampled synchronously with the clock, and then sent to the image forming unit 6. The image forming unit 6 forms a tomographic image (OCT image) of the eye to be examined E from the obtained interference signal.

In some embodiments, the main control unit 51 controls the drive unit 4D to perform the OCT measurement while revolving the optical system 2 within a predetermined angle range of movement by the swing mechanism 4B.

S3: Adjustment of Reference Position in Depth Direction

Next, the main control unit 51 adjusts the reference position of the measurement range in the depth direction (z-direction).

For example, the main control unit 51 makes the data processing unit 7 identify a predetermined site (for example, sclera) in the tomographic image obtained in step S2, and sets a position separated by a predetermined distance in the depth direction with respect to the position of the identified predetermined site as the reference position of the measurement range. The main control unit 51 controls a light path length changing unit (not illustrated) in accordance with the reference position. In addition, a predetermined position, which is determined in advance such that the optical path lengths of the measurement light and reference light substantially match each other, may be set as the reference position of the measurement range.

S4: Focus Adjustment, Polarization Adjustment

Next, the main control unit 51 performs focus adjustment control and polarization adjustment control.

For example, the main control unit 51 moves the focusing lens disposed between the scanning optical system 30 and the beam splitter M2 by a predetermined distance, and thereafter controls the scanning optical system 30 and the interference optical system 40 to perform the OCT measurement. As described above, the main control unit 51 causes the data processing unit 7 to determine the focus state of the measurement light based on the detection result of the interference light obtained by the OCT measurement. When the focus state of the measurement light is judges to be inappropriate based on the determination result by the data processing unit 7, the main control unit 51 performs the movement control of the focusing lens again and repeats it until the focus state is judged to be appropriate.

For example, the main control unit 51 controls a polarization controller (not illustrated) to change the polarization state of at least one of the light from the OCT light source and the measurement light by a predetermined amount; thereafter, the main control unit 51 controls the scanning optical system 30 and the interference optical system 40 to perform the OCT measurement, and causes the image forming unit 6 to form an OCT image based on the detection result of the interference light acquired. As described above, the main control unit 51 causes the data processing unit 7 to determine the image quality of the OCT image obtained by the OCT measurement. When the polarization state of the measurement light is judged to be inappropriate based on the determination result by the data processing unit 7, the main control unit 51 controls the polarization controller again and repeats it until the polarization state is judge to be appropriate.

S5: Acquisition of Interference Signal

Subsequently, the main control unit 51 controls the drive unit 4D to start revolving the optical system 2 within a predetermined angle range of movement by the swing mechanism 4B. Furthermore, the main control unit 51 controls the scanning optical system 30 and the interference optical system 40, during the revolution of the optical system 2, to perform the OCT measurement. The detection result of the interference light acquired by the OCT measurement is sampled at the DAQ and stored as an interference signal in the storage unit 52 or the like.

S6: Formation of Tomographic Image

Next, the main control unit 51 causes the image forming unit 6 to form a data set group of the A-scan image data of the eye to be examined E based on the interference signal acquired in step S5. The image forming unit 6 forms a tomographic image, as illustrated in FIG. 5, by arranging the formed A-scan images in the B-scan direction.

S7: Correction of Tomographic Image

The main control unit 51 corrects, as described above, the tomographic image formed in step S6 by using, for example, the eyeball parameter 52A stored in the storage unit 52. Details of step S7 will be described later. With this, as illustrated in FIG. 9, a tomographic image is acquired in which the A-scan images are arranged in the A-scan direction.

S8: Rotation of Tomographic Image

Next, the main control unit 51 identifies the swing amount and the swing direction by the swing mechanism 4B, and the tilt amount and the tilt direction by the tilt mechanism 4C, and determines the eccentric amount and the eccentric direction of the measurement optical axis O relative to the fovea from the identified swing amount and swing direction and the identified tilt amount and tilt direction. The main control unit 51 identifies the rotation angle and the rotation direction of the tomographic image from the determined eccentric amount and eccentric direction, and rotates the tomographic image corrected in step S7 at the identified rotation angle and in the identified rotation direction.

S9: Display

The display control unit 51A causes the display device to display the tomographic image rotated in step S8 (see FIG. 10). In some embodiments, the display control unit 51A causes a tomographic image to be displayed as illustrated in FIG. 11 or FIG. 12.

At this point, the operation of the ophthalmic device 1 is ended (END).

In step S7 of FIG. 13, the following process is performed as illustrated in FIG. 14.

S11: Calculation of Conversion Position

In step S7, the main control unit 51 makes the position identifying unit 71 identify a conversion position corresponding to a pixel position of the tomographic image having been formed in step S6. As described above, the position identifying unit 71 identifies the conversion position corresponding to the pixel position of the tomographic image.

S12: Conversion of Pixel Position

Subsequently, the main control unit 51 controls the position converting unit 72 to convert the pixel position of the tomographic image to the conversion position calculated in step S11.

S13: Next?

The main control unit 51 determines whether there is a pixel position to be converted next.

When it is determined that there is a pixel position to be converted next (S13: Y), the operation of the ophthalmic device 1 moves to step S11. When it is determined that there is no pixel position to be converted next (S13: N), the operation of the ophthalmic device 1 moves to step S14.

In steps S11 to S13, the identification of the conversion position and the conversion to the identified conversion position are performed for each pixel position of the tomographic image.

S14: Interpolation

When it is determined in step S13 that there is no pixel position to be converted next (S13: N), the main control unit 51 makes the interpolation unit 73 interpolate the pixels between the A-scan images adjacent to each other having been converted to the conversion positions in step S12.

At this point, the processing of step S7 in FIG. 13 is ended (END).

In the above operation example, a case is described in which the OCT measurement is performed by making the measurement optical axis O eccentric relative to the fovea of the eye to be examined E by using the swing mechanism 4B and the tilt mechanism 4C. However, the same applies to a case where the OCT measurement is performed by making the measurement optical axis O eccentric relative to the fovea of the eye to be examined E by changing a projection position of fixation light flux by the fixation optical system 50. In some embodiments, the OCT measurement is performed by making the measurement optical axis O eccentric relative to the fovea of the eye to be examined E by changing the projection position of the fixation light flux by the fixation optical system 50 while revolving the optical system 2 within a predetermined angle range of movement by using the swing mechanism 4B and the tilt mechanism 4C.

Modification Example

In the embodiment described above, a case is described in which a two-dimensional OCT image (or two-dimensional scan data) is corrected by coordinate transformation, but the configuration according to the embodiment is not limited thereto. The ophthalmic device according to the embodiment may correct a three-dimensional OCT image (or three-dimensional scan data) by coordinate transformation, similarly to the above-discussed embodiment. Hereinafter, an ophthalmic device according to a modification example of the embodiment will be described focusing on differences from the embodiment.

Since the configuration of the ophthalmic device according to the modification example of the embodiment is the same as the configuration of the ophthalmic device 1 according to the embodiment, description thereof will be omitted.

A data processing unit according to the present modification example performs identifying processing of a conversion position in a three-dimensional space, and the like.

The position identifying unit 71 according to the modification example identifies a conversion position along a traveling direction of the measurement light passing through the scanning center position Cs, where the conversion position corresponds to a pixel position in an OCT image acquired (or a scan position in scan data). In some embodiments, the position identifying unit 71 uses the eyeball parameter 52A to identify the conversion position.

Figure 15:
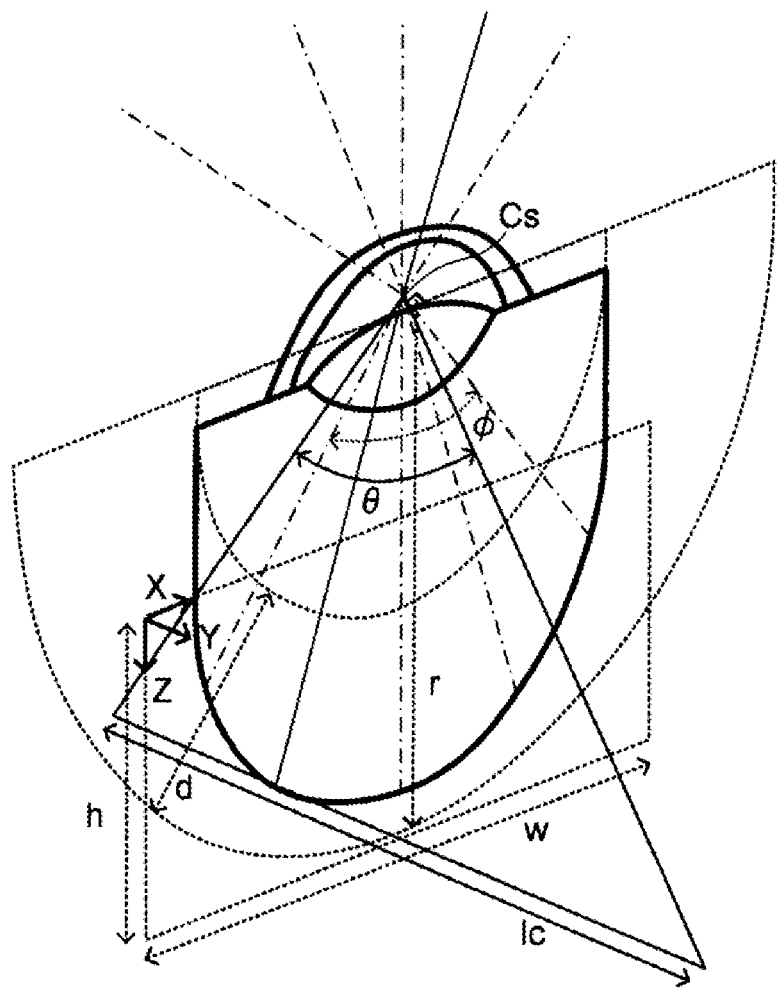
FIG. 15 is a schematic diagram for describing a process performed by an ophthalmic device according to a modification example of an embodiment.

FIG. 15 illustrates a descriptive diagram of operation of the position identifying unit 71 according to the modification example. In FIG. 15, constituent elements similar to those in FIG. 7 are denoted by the same reference signs, and description thereof will be omitted as appropriate.

In FIG. 15, a Y plane is defined, in addition to an X plane and a Z plane in FIG. 7. In addition to the parameters illustrated in FIG. 7, a center angle in a C-scan direction is denoted as θ, and a length in the C-scan direction is denoted as lc.

The position identifying unit 71 identifies a conversion position (X, Y, Z) in a fourth coordinate system from a pixel position (x, y, z) in a third coordinate system. The third coordinate system takes a coordinate position in the upper left corner of a three-dimensional OCT image as the origin, and is defined by an x-coordinate axis taking the B-scan direction as an x-direction, a y-coordinate axis that is orthogonal to the x-coordinate axis and takes the C-scan direction as a y-direction, and a z-coordinate axis that is orthogonal to both the x-coordinate axis and y-coordinate axis and takes the A-scan direction as a z-direction. The pixel position (x, y, z) in the OCT image is defined in the third coordinate system. The fourth coordinate system is defined by a Z coordinate axis taking, as a Z direction, the traveling direction of the measurement light with a scanning angle being 0 degrees relative to the measurement optical axis passing through a predetermined site (for example, the fovea) at the fundus Ef, an X coordinate axis taking, as an X direction, the B-scan direction orthogonal to the Z coordinate axis at the above predetermined site, and Y coordinate axis taking, as a Y direction, the C-scan direction orthogonal to the Z coordinate axis at the above predetermined site. In the fourth coordinate system, a predetermined Z position is taken as the origin of the Z coordinate axis in such a manner that the position of a scanning radius r is the deepest portion of the measurement optical axis passing through a predetermined site (for example, the fovea). In addition, as described below, predetermined X and Y positions of the measurement optical axis passing through a predetermined site (for example, the fovea) are taken as the origins of the X coordinate axis and Y coordinate axis respectively in such a manner as to bring a length d in a predetermined depth direction. The conversion position (X, Y, Z) is defined in the fourth coordinate system. The conversion position (X, Y, Z) corresponds to the pixel position (x, y, z), and is a position along the traveling direction (A-scan direction) of the measurement light passing through the scanning center position Cs.

The position identifying unit 71 is able to identify at least one of an X component, a Y component, and a Z component of the conversion position.

For the OCT image (tomographic image) where the number of A-scan lines is N (N is a natural number) and the number of B-scan lines is M (M is a natural number), the conversion position (X, Y, Z) corresponding to the pixel position (x, y, z) in the n-th A-scan line (n is a natural number) of the m-th B-scan line (m is a natural number) is identified as indicated by Equation (6) to Equation (8).

[Equation 6]

$$X = \frac{w}{2} + \frac{(r-d+z) \times \tan\left(\frac{\phi}{N} \times n - \frac{\phi}{2}\right)}{\sqrt{\tan^2\left(\frac{\phi}{N} \times n - \frac{\phi}{2}\right) + \tan^2\left(\frac{\theta}{M} \times m - \frac{\theta}{2}\right) + 1}} \quad (6)$$

[Equation 7]

$$Y = \frac{lc}{2} + \frac{(r-d+z) \times \tan\left(\frac{\theta}{M} \times m - \frac{\theta}{2}\right)}{\sqrt{\tan^2\left(\frac{\phi}{N} \times n - \frac{\phi}{2}\right) + \tan^2\left(\frac{\theta}{M} \times m - \frac{\theta}{2}\right) + 1}} \quad (7)$$

[Equation 8]

$$Z = \frac{(r-d+z)}{\sqrt{\tan^2\left(\frac{\phi}{N} \times n - \frac{\phi}{2}\right) + \tan^2\left(\frac{\theta}{M} \times m - \frac{\theta}{2}\right) + 1}} - (r-h). \quad (8)$$

From a length h in the depth direction, a length w in the B-scan direction, and the length lc in the C-scan direction of the three-dimensional OCT image, the x component and y component of the pixel position are expressed as in Equation (9) to Equation (13).

[Equation 9]

$$h = r - (r-d) \times \cos\frac{\phi}{2} \quad (9)$$

[Equation 10]

$$w = 2r \times \sin\frac{\phi}{2} \quad (10)$$

[Equation 11]

$$lc = 2r \times \sin\frac{\theta}{2} \quad (11)$$

[Equation 12]

$$x = n \quad (12)$$

[Equation 13]

$$y = m \quad (13)$$

In Equations (6) to (8), the x-coordinate and y-coordinate of the pixel position are expressed as in Equations (12) and (13). Accordingly, the position identifying unit 71 is able to identify the conversion position (X, Y, Z) from the pixel position (x, y, z) based on the scanning radius r, a scanning angle φ, and the depth range d.

In some embodiments, for the scan data, the position identifying unit 71 is able to identify the conversion position (X, Y, Z) in the same manner as described above.

The position converting unit 72 according to the modification example converts the pixel position (x, y, z) of the OCT image to the conversion position (X, Y, Z) identified by the position identifying unit 71. In some embodiments, for each of all the pixel positions in the OCT image, the position identifying unit 71 identifies the conversion position, and the position converting unit 72 converts the pixel position to the conversion position.

In the embodiment described above, a case is described in which a tomographic image is corrected by the ophthalmic device including the optical system 2 and the like, but the configuration according to the embodiment is not limited thereto. For example, an ophthalmic information processing device that implements the functions of the data processing unit 7 illustrated in FIG. 6 may correct a tomographic image in the manner as described above with respect to the acquired OCT image (or scan data), and may perform rotation processing on the corrected tomographic image based on the eccentric amount and the eccentric direction. In this case, the OCT image (or scan data) is acquired by an external OCT device (ophthalmic device).

In some embodiments, a program for causing a computer to perform a method for controlling the above-described ophthalmic device is provided. Such a program may be stored on any computer-readable recording medium. As the recording medium mentioned above, for example, a semiconductor memory, an optical disk, a magneto-optical disk (CD-ROM, DVD-RAM, DVD-ROM, MO, or the like), or a magnetic storage medium (hard disk, floppy (registered trademark) disk, ZIP, or the like) may be used. It is also possible to transmit and receive this program through a network such as the Internet or a LAN.

Effects

The ophthalmic information processing device, the ophthalmic device, the ophthalmic information processing method, and the programs according to the embodiment will be described below.

The ophthalmic information processing device (for example, the device including the data processing unit 7) according to some embodiments includes the image rotation unit (rotation unit 74) and the display control unit 51A. The image rotation unit rotates a tomographic image of the eye to be examined acquired by using optical coherence tomography while making the measurement optical axis O be eccentric relative to a predetermined site (the fovea or macular region) of the eye to be examined E, in accordance with the eccentric amount and eccentric direction of the measurement optical axis relative to the predetermined site. The display control unit causes the display device (display device of the UI unit 8) to display the tomographic image rotated by the image rotation unit.

According to the above configuration, since the tomographic image of the eye to be examined acquired by using the optical coherence tomography while making the measurement optical axis be eccentric relative to the predetermined site of the eye to be examined is caused to be rotated in accordance with the eccentric amount and the eccentric direction and displayed on the display device, it is easy to grasp the measurement position based on the predetermined site. As a result, it is possible to easily grasp the form of the fundus or the like of the eye to be examined being depicted in the tomographic image.

In some embodiments, the eccentric amount is determined by using at least one of the swing amount and the tilt amount of the optical system 2 configured to perform the optical coherence tomography based on the eye to be examined, and the eccentric direction is determined by using at least one of the swing direction and the tilt direction of the optical system based on the eye to be examined.

According to the above configuration, it is possible, by using any of the swing amount, swing direction, tilt amount and tilt direction, to rotate a tomographic image acquired while making the measurement optical axis be eccentric relative to a predetermined site of the eye to be examined by at least one of a swing motion and a tilt motion of the optical system based on the eye to be examined. As a result, it is possible to acquire a wide angle tomographic image, which makes it possible to easily grasp the form of the fundus or the like of the eye to be examined.

In some embodiments, the eccentric amount is determined by using a displacement amount of a projection position of fixation light flux relative to the measurement optical axis at the fundus Ef of the eye to be examined, and the eccentric direction is determined by using a displacement direction of the projection position relative to the measurement optical axis at the fundus.

According to the above configuration, it is possible, by using the displacement amount and displacement direction of the projection position, to rotate a tomographic image acquired while making the measurement optical axis be eccentric relative to a predetermined site of the eye to be examined by changing the projection position of the fixation light flux. As a result, it is possible to acquire a wide angle tomographic image, which makes it possible to easily grasp the form of the fundus or the like of the eye to be examined.

Some embodiments include the converting unit (position converting unit 72) configured to convert a pixel position of the tomographic image acquired by using the optical coherence tomography to a conversion position along the A-scan direction, and the image rotation unit rotates the tomographic image in which the pixel position has been converted to the conversion position by the converting unit.

According to the above configuration, it is possible to grasp the shape of the fundus or the like depicted in the tomographic image as the actual shape. As a result, it is possible to acquire a wide angle tomographic image, which makes it possible to easily grasp the actual form of the fundus or the like of the eye to be examined.

In some embodiments, the display control unit causes the display device to display the tomographic image IMG11 rotated by the image rotation unit in such a manner that the tomographic image IMG11 is superimposed on the image IMG10 representing a cross-sectional structure of the eye.

According to the above configuration, it is possible to recognize the measurement position at a glance, making it easy to grasp the shape and the like of a site inside the eye in relation to the cross-sectional structure of the eye.

In some embodiments, the display control unit adjusts the size of the image based on the tomographic image, and causes the display device to display the tomographic image IMG11 rotated by the image rotation unit in such a manner that the tomographic image IMG11 is superimposed on the image IMG10 having the adjusted size.

According to the above configuration, it is possible to recognize the measurement position at a glance, making it easy to grasp the shape and the like of a site inside the eye in relation to the cross-sectional structure of the eye.

The ophthalmic device 1 according to some embodiments includes the OCT unit (the scanning optical system 30, interference optical system 40, image forming unit 6, and data processing unit 7) configured to acquire, by using optical coherence tomography, a tomographic image of the eye to be examined while making the measurement optical axis be eccentric relative to a predetermined site of the eye to be examined, and the ophthalmic information processing device described in any one of the above embodiments.

According to the above configuration, it is possible to provide an ophthalmic device able to acquire a tomographic image that makes it easy to grasp the form of the fundus or the like of the eye to be examined.

Some embodiments include the swing mechanism 4B configured to move the optical system 2 for performing the optical coherence tomography in the horizontal direction based on the eye to be examined, and the swing mechanism causes the measurement optical axis to be eccentric relative to a predetermined site (the fovea or macular region) of the eye to be examined.

According to the above configuration, it is possible to provide an ophthalmic device able to acquire a wide angle tomographic image, which makes it possible to easily grasp the form of the fundus or the like of the eye to be examined with a simple configuration.

Some embodiments include the tilt mechanism 4C configured to move the optical system 2 for performing the optical coherence tomography in the vertical direction based on the eye to be examined, and the tilt mechanism causes the measurement optical axis to be eccentric relative to a predetermined site (the fovea or macular region) of the eye to be examined.

According to the above configuration, it is possible to provide an ophthalmic device able to acquire a wide angle tomographic image, which makes it possible to easily grasp the form of the fundus or the like of the eye to be examined with a simple configuration.

Some embodiments include the fixation optical system 50 configured to project fixation light flux onto a projection position that is changeable relative to the fundus Ef of the eye to be examined.

According to the above configuration, it is possible to provide an ophthalmic device able to acquire a wide angle tomographic image, which makes it possible to easily grasp the form of the fundus or the like of the eye to be examined with a simple configuration.

The ophthalmic information processing method according to some embodiments includes the image-rotating and the display-controlling. The image-rotating rotates a tomographic image of the eye to be examined acquired by using optical coherence tomography while making the measurement optical axis O be eccentric relative to a predetermined site (the fovea or macular region) of the eye to be examined E, in accordance with the eccentric amount and eccentric direction of the measurement optical axis relative to the predetermined site. The display-controlling causes the display device (display device of the UI unit 8) to display the tomographic image rotated by the image-rotating.

According to the above method, since the tomographic image of the eye to be examined acquired by using the optical coherence tomography while making the measurement optical axis be eccentric relative to the predetermined site of the eye to be examined is caused to be rotated in accordance with the eccentric amount and the eccentric direction and displayed on the display device, it is easy to grasp the measurement position based on the predetermined site. As a result, it is possible to easily grasp the form of the fundus or the like of the eye to be examined being depicted in the tomographic image.

In some embodiments, the eccentric amount is determined by using at least one of the swing amount and the tilt amount of the optical system 2 configured to perform the optical coherence tomography based on the eye to be examined, and the eccentric direction is determined by using at least one of the swing direction and the tilt direction of the optical system based on the eye to be examined.

According to the above method, it is possible, by using any of the swing amount, swing direction, tilt amount and tilt direction, to rotate a tomographic image acquired while making the measurement optical axis be eccentric relative to a predetermined site of the eye to be examined by at least one of the swing motion and the tilt motion of the optical system based on the eye to be examined. As a result, it is possible to acquire a wide angle tomographic image, which makes it possible to easily grasp the form of the fundus or the like of the eye to be examined.

In some embodiments, the eccentric amount is determined by using a displacement amount of a projection position of fixation light flux relative to the measurement optical axis at the fundus Ef of the eye to be examined, and the eccentric direction is determined by using a displacement direction of the projection position relative to the measurement optical axis at the fundus.

According to the above method, it is possible, by using the displacement amount and displacement direction of the projection position, to rotate a tomographic image acquired while making the measurement optical axis be eccentric relative to a predetermined site of the eye to be examined by changing the projection position of the fixation light flux. As a result, it is possible to acquire a wide angle tomographic image, which makes it possible to easily grasp the form of the fundus or the like of the eye to be examined.

In some embodiments, the display-controlling causes the display device to display the tomographic image IMG11 rotated by the image-rotating in such a manner that the tomographic image IMG11 is superimposed on the image IMG10 representing a cross-sectional structure of the eye.

According to the above method, it is possible to recognize the measurement position at a glance, making it easy to grasp the shape and the like of a site inside the eye in relation to the cross-sectional structure of the eye.

The program according to some embodiments causes a computer to execute the image-rotating and the display-controlling of the ophthalmic information processing method described in any one of the embodiments.

According to the above program, since the tomographic image of the eye to be examined acquired by using the optical coherence tomography while making the measurement optical axis be eccentric relative to the predetermined site of the eye to be examined is caused to be rotated in accordance with the eccentric amount and the eccentric direction and displayed on the display device, it is easy to grasp the measurement position based on the predetermined site. As a result, it is possible to easily grasp the form of the fundus or the like of the eye to be examined being depicted in the tomographic image.

Others

The embodiments or the modification example thereof described above are merely examples for carrying out the invention. Any deformation, omission, addition, or the like may be made by those intending to carry out the invention within the scope of the invention.

What is claimed is:

1. An ophthalmic information processing device comprising: an image rotation circuit configured to rotate a tomographic image of an eye to be examined, the tomographic image being acquired by using optical coherence tomography while making a measurement optical axis be eccentric relative to a predetermined site of the eye to be examined in accordance with an eccentric amount and an eccentric direction of the measurement optical axis relative to the predetermined site; a display control circuit configured to cause a display device to display the tomographic image rotated by the image rotation circuit in such a manner as to superimpose the tomographic image rotated by the image rotation circuit on a model image representing a cross-sectional structure of the eye, and wherein the model image is generated based on at least one of a drawing of an eye, an illustration of an eye, a model of an eye, a photograph of an eye, and a video of an eye.

2. The ophthalmic information processing device according to claim 1,
wherein the eccentric amount is determined by using at least one of a swing amount and a tilt amount of an optical system configured to perform the optical coherence tomography based on the eye to be examined, and
the eccentric direction is determined by using at least one of a swing direction and a tilt direction of the optical system based on the eye to be examined.

3. The ophthalmic information processing device according to claim 1,
wherein the eccentric amount is determined by using a displacement amount of a projection position of fixation light flux relative to the measurement optical axis at a fundus of the eye to be examined, and
the eccentric direction is determined by using a displacement direction of the projection position relative to the measurement optical axis at the fundus.

4. The ophthalmic information processing device according to claim 1, further comprising:
a converting circuit configured to convert a pixel position of the tomographic image acquired by using the optical coherence tomography to a conversion position along an A-scan direction,
wherein the image rotation circuit rotates the tomographic image in which the pixel position is converted to the conversion position by the converting circuit.

5. The ophthalmic information processing device according to claim 1,
wherein the display control circuit adjusts a size of the model image based on the tomographic image, and causes the display device to display the tomographic image rotated by the image rotation circuit in such a manner as to superimpose the tomographic image on the model image having the adjusted size.

6. The ophthalmic information processing device according to claim 1, wherein the model image is generated based on another eye.

7. An ophthalmic device comprising: an optical coherence tomography (OCT) sensor configured to acquire a tomographic image of the eye to be examined by using optical coherence tomography while making a measurement optical axis be eccentric relative to a predetermined site of the eye to be examined; an image rotation circuit configured to rotate a tomographic image of an eye to be examined, the tomographic image being acquired by using optical coherence tomography while making a measurement optical axis be eccentric relative to a predetermined site of the eye to be examined in accordance with an eccentric amount and an eccentric direction of the measurement optical axis relative to the predetermined site; a display control circuit configured to cause a display device to display the tomographic image rotated by the image rotation circuit in such a manner as to superimpose the tomographic image rotated by the image rotation circuit on a model image representing a cross-sectional structure of the eye, and wherein the model image is generated based on at least one of a drawing of an eye, an illustration of an eye, a model of an eye, a photograph of an eye, and a video of an eye.

8. The ophthalmic device according to claim 7, further comprising:
a swing mechanism configured to move an optical system for performing the optical coherence tomography in a horizontal direction based on the eye to be examined,
wherein the swing mechanism causes the measurement optical axis to be eccentric relative to a predetermined site of the eye to be examined.

9. The ophthalmic device according to claim 7, further comprising:
a tilt mechanism configured to move the optical system for performing the optical coherence tomography in a vertical direction based on the eye to be examined,
wherein the tilt mechanism causes the measurement optical axis to be eccentric relative to a predetermined site of the eye to be examined.

10. The ophthalmic device according to claim 7, further comprising:

a fixation optical system configured to project fixation light flux onto a projection position that is changeable relative to the fundus of the eye to be examined.

11. An ophthalmic information processing method comprising: image-rotating a tomographic image of an eye to be examined acquired by using optical coherence tomography while making a measurement optical axis be eccentric relative to a predetermined site of the eye to be examined in accordance with an eccentric amount and an eccentric direction of the measurement optical axis relative to the predetermined site; display-controlling to cause a display device to display the tomographic image rotated by the image-rotating in such a manner as to superimpose the tomographic image rotated by the image-rotating on a model image representing a cross-sectional structure of the eye, and wherein the model image is generated based on at least one of a drawing of an eye, an illustration of an eye, a model of an eye, a photograph of an eye, and a video of an eye.

12. The ophthalmic information processing method according to claim 11,
wherein the eccentric amount is determined by using at least one of a swing amount and a tilt amount of an optical system configured to perform the optical coherence tomography based on the eye to be examined, and
the eccentric direction is determined by using at least one of a swing direction and a tilt direction of the optical system based on the eye to be examined.

13. The ophthalmic information processing method according to claim 11,
wherein the eccentric amount is determined by using a displacement amount of a projection position of fixation light flux relative to the measurement optical axis at a fundus of the eye to be examined, and
the eccentric direction is determined by using a displacement direction of the projection position relative to the measurement optical axis at the fundus.

14. A non-transitory computer storage medium storing a program to be executed by a computer including steps of: image-rotating a tomographic image of an eye to be examined acquired by using optical coherence tomography while making a measurement optical axis be eccentric relative to a predetermined site of the eye to be examined in accordance with an eccentric amount and an eccentric direction of the measurement optical axis relative to the predetermined site; display-controlling to cause a display device to display the tomographic image rotated by the image-rotating in such a manner as to superimpose the tomographic image rotated by the image-rotating on a model image representing a cross-sectional structure of the eye, and wherein the model image is generated based on at least one of a drawing of an eye, an illustration of an eye, a model of an eye, a photograph of an eye, and a video of an eye.

* * * * *